United States Patent
Gleason et al.

(10) Patent No.: US 10,888,104 B2
(45) Date of Patent: Jan. 12, 2021

(54) FATTY ACID COMPOSITION AND METHOD FOR FORTIFYING NUTRITIONAL PRODUCTS WITH FATTY ACIDS

(71) Applicant: JOST CHEMICAL CO., St. Louis, MO (US)

(72) Inventors: John Gleason, St. Louis, MO (US); Douglas Caskey, Overland, MO (US); Eric Bruton, Lake St. Louis, MO (US); Teresa Bandrowsky, St. Louis, MO (US); Douglas Jost, St. Louis, MO (US)

(73) Assignee: Jost Chemical Co., St. Louis, MO (US)

( * ) Notice: Subject to any disclaimer, the term of this patent is extended or adjusted under 35 U.S.C. 154(b) by 67 days.

(21) Appl. No.: 15/513,377

(22) PCT Filed: Sep. 22, 2015

(86) PCT No.: PCT/US2015/051437
§ 371 (c)(1),
(2) Date: Mar. 22, 2017

(87) PCT Pub. No.: WO2016/049018
PCT Pub. Date: Mar. 31, 2016

(65) Prior Publication Data
US 2020/0022394 A1 Jan. 23, 2020

Related U.S. Application Data

(60) Provisional application No. 62/054,178, filed on Sep. 23, 2014.

(51) Int. Cl.
*A23L 33/12* (2016.01)
*A23L 33/16* (2016.01)
*A23L 33/15* (2016.01)
*C07C 51/41* (2006.01)

(52) U.S. Cl.
CPC ........... *A23L 33/12* (2016.08); *A23L 33/15* (2016.08); *A23L 33/16* (2016.08); *C07C 51/41* (2013.01)

(58) Field of Classification Search
CPC .......... A23L 33/12; A23L 33/16; A23L 33/15; C07C 51/41
USPC ........... 426/72, 648, 98, 601, 656, 801, 519
See application file for complete search history.

(56) References Cited

U.S. PATENT DOCUMENTS

| | | |
|---|---|---|
| 2,851,358 A | 9/1958 | McCarthy |
| 2,928,742 A | 3/1960 | Kennedy et al. |
| 2,994,612 A | 8/1961 | Rice |
| 3,185,580 A | 5/1965 | Hanrahan et al. |
| 4,031,263 A | 6/1977 | Kalopissis et al. |
| 4,318,932 A | 3/1982 | Ewing et al. |
| 4,399,128 A | 8/1983 | Hirsbrunner |
| 4,692,338 A | 9/1987 | Irvine et al. |
| 5,244,681 A | 9/1993 | Vinci et al. |
| 5,397,589 A | 3/1995 | Korte et al. |
| 5,518,751 A | 5/1996 | de Boer et al. |
| 5,658,767 A | 8/1997 | Kyle |
| 5,976,606 A | 11/1999 | Koga et al. |
| 5,990,164 A | 11/1999 | Horrobin et al. |
| 6,531,150 B1 * | 3/2003 | Sunohara et al. |
| 7,138,431 B1 | 11/2006 | Chilton |
| 2004/0191294 A1 | 9/2004 | Ramaprasad et al. |
| 2006/0160891 A1 | 7/2006 | Fukami |
| 2008/0145475 A1 | 6/2008 | Flatt et al. |
| 2009/0182050 A1 | 7/2009 | Barrow et al. |
| 2009/0221705 A1 | 9/2009 | Rongved et al. |
| 2009/0304854 A1 | 12/2009 | Peterson et al. |
| 2011/0039932 A1 | 2/2011 | Luchini et al. |
| 2011/0287140 A1 * | 11/2011 | Moonen et al. |
| 2012/0116106 A1 | 5/2012 | Gleason et al. |
| 2012/0171350 A1 | 7/2012 | Lai et al. |
| 2014/0249224 A1 * | 9/2014 | Lai et al. |

FOREIGN PATENT DOCUMENTS

| | | |
|---|---|---|
| AU | 2003203973 A1 | 10/2004 |
| CN | 1135290 A | 11/1996 |
| CN | 102599260 A | 7/2012 |

(Continued)

OTHER PUBLICATIONS

Chen et al. "Co-encapsulation of fish oil with phytosterol esters and limonene by milk proteins", Journal of Food Engineering, vol. 117 (2013), pp. 505-512.*
International Search Report, dated Dec. 21, 2015 from corresponding PCT/US2015/051437.
Written Opinion, dated Dec. 21, 2015 from corresponding PCT/US2015/051437.
Finley et al., Breast Milk Composition: Fat Content and Fatty Acid Composition in Vegetarians and Non-Vegetarians, the American Journal of Clinical Nutrition, vol. 41, Apr. 1985, pp. 787-800.

(Continued)

*Primary Examiner* — Helen F Heggestad
(74) *Attorney, Agent, or Firm* — Sandberg Phoenix & von Gontard, PC

(57) ABSTRACT

A fatty acid composition is provided which can be used to make fatty acid fortified nutritional products. In one embodiment, the fatty acid composition comprises a fatty acid component, inorganic salts (which can include a phosphate salt), vitamins, and optionally a protein source and optionally a carbohydrate source. The composition can further include additional nutrients and combinations thereof. In another embodiment, the fatty acid composition is only the fatty acid (i.e., consists of a sodium or potassium fatty acid) which is spray dried. In both embodiments, the fatty acid composition is not microencapsulated in a waxy or carbohydrate substrate, yet the powdered composition is flowable and is easily dispersible in a liquid to form a stable dispersion in the liquid by stirring or shaking the powder in the liquid for only a short period of time.

51 Claims, No Drawings

(56) References Cited

FOREIGN PATENT DOCUMENTS

| CN | 103458708 A | 12/2013 | |
|---|---|---|---|
| GB | 654722 | 6/1951 | |
| GB | 955347 | 4/1964 | |
| JP | H11146770 A | 2/1999 | |
| JP | 11146770 H | 6/1999 | |
| WO | 2007071261 A2 | 6/2007 | |
| WO | WO 2010/035704 | * | 4/2019 |

OTHER PUBLICATIONS

Bugeat et al., Enrichment in unsaturated fatty acids and emulsion droplet size affect the crystallization behaviour of milk triacylglycerols upon storage at 4° C.; Food Research International, vol. 44, 2011, pp. 1314-1330.

Montes et al., Effects of Drying and Aggolmeration on the Dissolution of Multi-Component Food Powders, Chemical Engineering Tech., 2011, vol. 34 No. 7, pp. 1159-1163.

Fonseca et al., Physical properties of goat milk powder with soy lecithin added before spray drying, International Journal of Science & Technology, 2011, vol. 46, pp. 608-611.

Koch et al. Basis of stability of Amine salts of Linoleic Acid, Journal of Food Science, vol. 36, 1971, pp. 477-481.

Kolanowski et al., Evaluation of sensory quality of instant foods fortified with omega-3 PUFA by addition of fish oil powder, European Food Research and Tech., Jan. 2007, pp. 715-721.

Nan Fu et al., Colloidal transport phenomena of milk components during convective droplet drying, Colloids and Surfaces B: Biointerfaces, vol. 87, 2011, pp. 255-266.

Extended European Search Report from corresponding EP Application No. 15843293 dated Mar. 15, 2018.

Office Action Issued for Corresponding Chinese Application No. CN103458708 dated Dec. 4, 2019.

* cited by examiner

FATTY ACID COMPOSITION AND METHOD FOR FORTIFYING NUTRITIONAL PRODUCTS WITH FATTY ACIDS

CROSS-REFERENCE TO RELATED APPLICATIONS

This application is the National Stage application of International App. No. PCT/US2015/051437 under 35 USC § 371 et seq. which claims priority to U.S. Pat. App. No. 62/054,178 entitled "Composition and Method for Fortifying Liquids with Fatty Acid Salts" which was filed on Sep. 23, 2014 and which is incorporated herein by reference.

STATEMENT REGARDING FEDERALLY SPONSORED RESEARCH OR DEVELOPMENT

Not Applicable.

FIELD OF THE INVENTION

This invention relates to methods of preparing a fatty acid composition which can be used to fortify human consumable liquids, semi-liquids and semi-solid foods and to the composition prepared by the disclosed methods. In addition, methods of using the disclosed composition are also disclosed.

BACKGROUND OF THE INVENTION

It has been known that increased dietary levels of certain fatty acids, particularly polyunsaturated fatty acids (PUFAs), have beneficial health effects. Some of the more common sources of unsaturated fatty acids include fish and marine oils, fungi, microalgae, and eggs. Examples of polyunsaturated fatty acids include: arachidonic acid (ARA), linoleic acid, alpha-linolenic acid (ALA), eicosapentaenoic acid (EPA), docosapentaenoic acid (DPA), eicosatetraenoic acid, moroctic acid, heneicosapentaenoic acid, and docosahexaenoic acid (DHA).

The evidence of the benefits of omega-3 and omega-6 polyunsaturated fatty acids, specifically DHA and ARA, in fetal and young children (i.e., infants and toddlers) for brain and retinal development are well documented. ((a) Belkind-Gerson, J.; Carreón-Rodriguez, A; Contreras-Ochoa, C. O.; Estrada-mondaca, S.; Parra-Cabrera, M. S. *Journal of Pediatric Gastroenterology and Nutrition* 2008, 47, S7-S9 and (b) Agostoni, C. *Journal of Pediatric Gastroenterology and Nutrition* 2008, 47, S41-S44). Docosahexaenoic acid (DHA) and arachidonic acid (ARA) are major fatty acids present in the structural phospholipids of the human brain and retina. Human breast milk naturally contains omega-3 and omega-6 fatty acids and while feeding infants with breast milk may be the best alternative, supplemental fatty acids in infant formula have been shown to be as bioavailable as the fatty acids in breast milk. (Sala-Vila, A. et al *Journal of Nutrition* 2004, 134 868-873).

Supplementation of unsaturated fatty acids such as EPA and DHA have been of particular interest to the food industry for many years due to evidence that increasing dietary levels of unsaturated fatty acids has beneficial effects on health in adults. It is well established in the medical community that both EPA and DHA can lower serum triglycerides. Numerous clinical studies have also shown that even low doses of these fatty acids extend cardiovascular benefits such as greater protection from heart disease and cardiac arrhythmias, lowering blood pressure, and improving diabetic biochemistry. There is mounting evidence of additional benefits related to protection and treatment of inflammation, neurodegenerative diseases, and cognitive development.

Unsaturated fatty acids such as EPA, DHA, and ARA can be synthesized by the human body in limited amounts. However, sources of these fatty acids are primarily derived from dietary sources. Diets rich in fish oils are known to have beneficial effects on the prevention of cardiovascular diseases, chronic diseases, and even cancer. Despite such evidence of the benefits of these fatty acids, daily consumption of sources rich in these fatty acids is low. Since it is difficult to alter an individual's diet, an important approach to the issue of increasing fatty acid consumption is supplementation. Unfortunately, many forms of fatty acid supplements are sensitive to oxidation. Oxidative degradation can lead to the development of off-flavors, particularly rancid or fishy smell and taste. Initially, most sources of the acid are free of these off-flavors; however, oxidation occurs rapidly in the presence of air. The off-flavors from many fatty acid containing products have limited their incorporation into a wider range of products.

Fatty acid triglycerides or ethyl esters (common forms of PUFAs in the market) do not dissolve or disperse readily in aqueous liquids (such as water, milk products or other drink mixes). Traditionally, microencapsulation has been used to incorporate PUFAs into food, nutraceutical, and pharmaceutical products. Microencapsulated PUFAs aid in slowing oxidation degradation, mask undesirable flavors and/or odors, improve matrix compatibility, improve dispersion, and enhance stability.

Traditional microencapsulation of PUFAs provides a solid form of triglycerides or ethyl esters which also aids in handling and formation of food beverages, semi-liquid and milk products. It also improves dispersion and/or suspension of the triglycerides or ethyl esters in food and beverages, and especially in liquids and semi-liquids, such as milk and milk products. Despite such improvements, traditionally microencapsulated PUFAs are limited in many areas, but specifically in the area of semi-liquids and milk products with regards to solubility, load, and reconstitution of a dry blend. Thus, traditional microencapsulation limits the content of fatty acid that can be integrated into these forms. This traditional or intentional microencapsulation is to be distinguished from in-situ microencapsulation or substance segregation, wherein, during drying one component of a composition can, in effect, migrate to the surface of the composition, such that one component of the composition, in effect, encapsulates another component of the composition.

Typical loads for traditionally microencapsulated PUFAs utilize sugars, starches, preservatives, flavors and similar ingredients to achieve a 5% to 20% load. (Hannah, 2009 & Conto et. al., 2012). Thus the concentration in a traditionally microencapsulated PUFA product is very low with respect to the product weight. This means that the majority of the microencapsulated product is composed of additives such as maltodextrin, glucose, sugar derivatives, starch, gelatin, plant gums, and similar types of ingredients. Such formulations allow for only low concentrations of the PUFAs in the microencapsulated product. The additional materials (i.e., wall or shell materials) used to microencapsulate fatty acids (in the triglyceride form) are particularly relevant with respect to infant formula and functional foods as they affect the composition of the product in terms of fat, protein, and sugar content. This low concentration of PUFA's must be accounted for in product formulation. This is especially important for infant formula because it may be the only source of food for an infant and as such needs to contain the right balance of nutrients. The components of some currently available microencapsulated PUFA formulations are shown in the table below.

| Ingredients | DSM Life's DHA Microencapsulation Algal Vegetable Oil | Cargill-Alking Bioengineering Arachidonic Acid Powder | BASF Dry n-3 5:25 C | BASF Dry n-3 12 Food |
|---|---|---|---|---|
| DHA Algal Oil | X | | | |
| ARA Oil | | X | | |
| Fish Oil | | | X | X |
| Glucose Syrup Solids | X | X | | |
| Saccharose | | | X | X |
| Maltodextrin | | X | | |
| Sodium Caseinate (Milk) | X | X | X | X |
| Starch | | | X | X |
| Modified starch | | X | | |
| Soy Protein | X | | | |
| High Oleic Sunflower Oil | X | | | |
| Sodium Ascorbate | X | X | X | X |
| Tricalcium Phosphate | X | X | X | X |
| Tetrasodium Diphosphate | X | | | |
| Natural Flavors | X | | | |
| Lecithin | X | | X | X |
| Mixed Natural Tocopherols | X | | X | X |
| Mono-and-diglycerides | | | X | X |
| Sodium citrate | | X | | |
| Ascorbyl Palmitate | X | | X | X |

In traditionally microencapsulated PUFAs, the PUFA is encased, surrounded, or coated with a selected shell or wall material which does not form an active component of the encapsulated product. As discussed below, our fatty acid composition is not microencapsulated in this traditional sense. That is, it is not subject to a microencapsulation step which encases the fatty acid component of the composition in a waxy or carbohydrate substrate that is not otherwise an active component of the composition. Our composition has several desirable advantages over the traditionally microencapsulated PUFAs. As discussed more fully below, our fatty acid component is instantizable and generates a stable dispersion with little or no load issue. Further, our fatty acid composition has a similar profile to the microencapsulated PUFAs. Because of these attributes, for oxidative degradation, odor, taste and stability the fatty acid composition may provide superior performance in many formulations.

Infants need both ARA and DHA (DPA may also be used in the diet), and adults typically benefit from dietary supplementation of EPA and DHA. Due to the need for omega-3 and omega-6 fatty acids in the infant diet, as well as in young children and adult diets, increasing consumer demand for food and food supplements containing unsaturated fatty acids, the need exists for a method that allows for ease of incorporation of these valuable fatty acids into food and beverages without undesirable changes in flavor, texture, appearance, shelf life, or nutritional profile.

BRIEF SUMMARY OF THE INVENTION

In accordance with the purposes of the disclosed materials, components, compositions and methods, as embodied and broadly described herein, the present invention, in one aspect, relates to fatty acid compositions and methods for preparing and using such compositions. In a further aspect, the invention relates to methods of preparing salts of fatty acids (e.g., omega-3 and omega-6 fatty acids). In yet another aspect, the invention relates to compositions prepared by the methods disclosed herein. Also disclosed are methods of using the disclosed fatty acid compositions.

The present invention describes a fatty acid component comprising fatty acid salts that in a powder form readily (and almost instantaneously) disperse in liquids, such as, for example, water, milk, milk substitutes, milk products, milk-like products (such as infant formula, meal replacement shakes, breakfast drinks, and protein shakes, etc.) and can be incorporated into semi-liquid or even semi-solid food products (such as gelatins, puddings, doughs, etc.). The basic fatty acid component is readily dispersible without formulation; however, the fatty acid component may also be incorporated in a fatty acid composition to improve processing for some applications, provide additional nutrients, and to improve shelf-life. The fatty acid component exhibits emulsifying properties and forms stable suspensions. Many insoluble salts such as calcium and magnesium fatty acid salts can form difficult to disperse sediments in solution. We have found that the fatty acid component can stabilize such suspensions and take the place of stabilizers such as, for example, carrageenan, which would otherwise be needed in such suspensions.

Importantly, the fatty acid composition provides bioavailable free fatty acids that are easily digested and absorbed, that have good organoleptic properties, and that are provided in a stable powder form. Further, the fatty acid composition disperses quickly and easily in aqueous liquids, such as water, milk, formula and milk substitutes, without the need for traditional microencapsulation. Thus, the fatty acid composition is not subject to traditional microencapsulation.

Sources of fatty acids are typically obtained as oils in the form of glycerides, esters, or phospholipids. As a result, the free acid is comprised of a mixture of multiple fatty acids. The fatty acid component can be derived or prepared from fish or the marine oils isolated from marine life. One or more of these fatty acids can be converted to their corresponding salt by the methods disclosed herein. Any fish oil, marine oil, or combination thereof can be used in the disclosed methods to prepare the disclosed fatty acid component or compositions. In another aspect, the fatty acid component can be derived from vegetables, plants, animals, and edible oils. In specific examples, the fatty acid component can be derived from fungi, microalgae, or eggs. Any derivative or combination of these oils can also be used. The fatty acid component may also be processed to result in a particular mixture of fatty acids (e.g., having only saturated fatty acids, only unsaturated fatty acids, or mixtures thereof). It is anticipated that the amount of saturated fatty acids will be about 10 to 35 weight percent.

The production of the fatty acid component only converts the free fatty acids to their corresponding salt forms, hence the fatty acid component is also comprised of a mixture of fatty acid salts that are present in the naturally occurring triglyceride or ester oil source or starting material. In one aspect, the disclosed fatty acid component can be prepared directly or indirectly from a starting material containing a fatty acid thereof or the free fatty acid. Such methods include, for example, situations where a fatty acid or a fatty acid ester is converted to its corresponding salt, or where one fatty acid salt is converted into another fatty acid salt.

The percentage of the fatty acids of interest, such as ARA or DHA, is determined by the content of that particular fatty acid within the original triglyceride or ester oil. The oils used in the disclosed compositions have a high concentration of the fatty acids, such as ARA, DHA, DPA and EPA, which are of particular interest.

In accordance with one aspect, a fatty acid composition is provided for making fatty acid fortified liquid products. The composition may be formulated to include only the ingredients described herein, or may be modified with optional ingredients to form a number of different product forms. The fatty acid composition may comprise just a fatty acid component or a fatty acid component in combination with a source of vitamins, inorganic salts, protein, and carbohydrates. These fortified liquid products which include the fatty acid composition are typically stable dispersions formed by stirring or shaking the fatty acid composition powder in the liquid.

The fatty acid of the fatty acid component is selected from arachidonic acid, C20:4 (n-6) (ARA), linoleic acid, C18:2 (n-6), alpha-linolenic acid, C18:3 (n-3) (ALA), eicosapentaenoic acid, C20:5 (n-3) (EPA), docosapentaenoic acid, C22:5 (n-3) (DPA), eicosatetraenoic acid, C20:4 (n-3), moroctic acid, C18:4(n-3), heneicosapentaenoic acid, C21:5(n-3), docosahexaenoic acid, C22:6 (n-3) (DHA), and combinations thereof. Non-limiting examples of suitable additional sources of fatty acids include corn oil, coconut oil, high oleic sunflower oil, soybean oil, medium chain triglycerides (MCT) oil, safflower oil, high oleic safflower oil, palm oil, palm kernel oil, olive oil, oleic acids, canola oil, and mixtures and combinations thereof.

In accordance with one aspect of the fatty acid composition, the fatty acid of the fatty acid component is a long-chain polyunsaturated fatty acid (LCPUFA's) of 18-carbon chains or longer containing at least two, and preferably at least four, double bonds.

In accordance with one aspect of the fatty acid composition, the fatty acid component is ARA and/or DHA. In particular, the fatty acid component can be a sodium or potassium salt of ARA and/or DHA.

In accordance with an aspect of the fatty acid composition, the fatty acid is derived from a source of fatty acids. The fatty acid composition comprises about 24% to about 90% by weight of the desired fatty acid.

In accordance with a specific formulation of the fatty acid composition, the fatty acid composition can be about 50% by weight of the desired fatty acid component.

The fatty acid component comprises a fatty acid salt with a monovalent cation chosen from the group consisting of sodium, potassium, ammonium, and the free base form of choline, lecithin, alanine, arginine, asparagine, aspartic acid, cysteine, glutamic acid, glutamine, glycine, ornithine, proline, selenocysteine, serine, tyrosine, histidine, isoleucine, leucine, lysine, methionine, phenylalanine, threonine, tryptophan, valine, and combinations thereof.

In accordance with one aspect of the fatty acid composition, the fatty acid component is a sodium or potassium salt of the fatty acid.

In accordance with one aspect of the fatty acid composition, the vitamins of the fatty acid composition may be chosen from vitamin C, vitamin A, vitamin E, vitamin D, vitamin K, vitamin B12, choline, folic acid, thiamine, riboflavin, carotenoids, niacin, pantothenic acid, biotin, mixed isomers of tocopherol, their salts and derivatives and combinations thereof. In a preferred embodiment, the vitamin is vitamin C, vitamin E, their salts or derivatives, and combinations thereof.

In accordance with an aspect of the fatty acid composition, the fatty acid composition is about 3% vitamins. In accordance with an aspect of the fatty acid composition, the fatty acid composition is about 1% by weight vitamins.

In accordance with one aspect of the fatty acid composition, inorganic salts of the fatty acid composition, may be chosen from citric acid and its derivatives and optionally from phosphate sources such as dibasic sodium phosphate, tetrasodium diphosphate, tricalcium phosphate, dibasic potassium phosphate, tetrapotassium diphosphate, ammonium phosphate salt, and combinations thereof.

In accordance with an aspect of the fatty acid composition, an inorganic salt, such as a phosphate salt, may be included with the fatty acid component to improve flow properties. The ratio of desired fatty acid to phosphate salt is about 0.3:1 to about 99:1. In an embodiment, the ratio of desired fatty acid to phosphate source is about 0.9:1 to about 10.4:1.

In accordance with an aspect of the fatty acid composition, the fatty acid composition may optionally comprise protein in addition to the fatty acid component. Any protein source that is suitable for use in nutritional products and is compatible with the elements of such products is suitable for use in combination with the fatty acid component. Non-limiting examples of suitable protein sources, if used, include skim milk powder, whole milk powder, nonfat milk powder, casein, caseinates, soy protein isolate, pea protein isolate, their derivatives, and combinations thereof. Other sources of protein can be used as well.

In accordance with an aspect of the fatty acid composition, the fatty acid composition may optionally comprise a carbohydrate source. Any carbohydrate source that is suitable for use in nutritional products and is compatible with the elements of such products is suitable for use in combination with the fatty acid component. Non-limiting examples of suitable carbohydrate sources, if used, may include maltodextrin, sugar, modified sugar, glucose, modified starch or cornstarch, corn syrup or solids, rice-derived carbohydrates, various vegetable-derived carbohydrates, sugar alcohols, artificial sweeteners, and combinations thereof.

In accordance with an aspect of the fatty acid composition, the fatty acid composition may comprise by weight about 63% to about 90% fatty acid component; about 0.5% to about 3% vitamins; about 0.5% to about 32% inorganic salts wherein about 0% to about 32% of the inorganic salts comprise phosphate salts, 0% to about 25% of a protein, and 0% to about 30% carbohydrates.

In accordance with an aspect of the fatty acid composition, the fatty acid composition comprises, by weight, about 10% to about 99% fatty acid component, 0.5% to about 50% inorganic salts, 0.5% to about 3% vitamins, 0% to about 50% carbohydrates, and 0% to about 30% of a protein source.

In accordance with an aspect of the fatty acid composition, the fatty acid composition does not include milk powder and the fatty acid composition is added to liquid milk, a milk-based food product, or a liquid milk-substitute to form a fatty acid fortified milk-based beverage. Without milk powder, the fatty acid composition is substantially free of protein.

In accordance with an aspect of the fatty acid composition, the fatty acid composition comprises milk powder and the fatty acid composition can be added to water to form a fatty acid fortified milk-based beverage. In this instance, the fatty acid composition can be 25% by weight milk powder. The amount of milk powder in the fatty acid composition could be altered if desired.

In accordance with an aspect of the invention, a fatty acid fortified milk product is provided. The fortified milk product comprises milk or a milk substitute and a fatty acid composition which is already dispersed in the milk or milk substitute and has formed a stable dispersion therein. The fatty acid composition is the composition as described above.

In accordance with another aspect of the invention, a fatty acid fortified infant formula is provided. The fortified infant formula comprises infant formula combined (mixed) with the fatty acid composition described above.

In one aspect of the fortified infant formula, both the infant formula and the fatty acid composition are in powder form. In this instance, the infant formula and fatty acid composition powder are added to a liquid, such as water, and dispersed therein.

In one aspect of the fortified infant formula, the fatty acid component is present in the infant formula in an amount such that the fortified infant formula has a fat content of between about 2.3% (23.6 g/L) and about 5.0% (50.0 g/L). In this instance, the fatty acid composition is between about 20% and about 50% by weight of the desired fatty acid component and the fatty acid component and milk solids are present in the fortified infant formula in a ratio of about 1:100 to about 1:1200. The infant formula powder and the fatty acid composition powder are mixed in a ratio of about 50:1 to about 600:1.

In accordance with a further aspect of the fatty acid fortified infant formula, the fatty acid component is selected from the above-noted list of fatty acids.

In accordance with an aspect of the fortified infant formula, the fatty acid component is an ARA or DHA salt which is present in an amount approximately equal to the amount of ARA or DHA in human breast milk.

In accordance with an aspect of the method of fortifying infant formula, the fatty acid component is an ARA or DHA salt. In particular, the fatty acid component can be Na-ARA, K-ARA, Na-DHA or K-DHA.

In accordance with a further aspect of the invention, a method of fortifying an infant formula with a fatty acid component is provided. The method comprises adding a fatty acid composition to an infant formula in an amount sufficient to provide a selected fatty acid content which corresponds to the amount of the selected fatty acid present in human breast milk. The method comprises mixing the fatty acid composition with the infant formula, for example, by stirring or shaking for less than one minute, whereby a stable dispersion of the fatty acid composition in the infant formula is formed. The fatty acid composition is the fatty acid composition as described above.

In accordance with a further aspect of the invention, a method is provided for providing a human with supplemental fatty acids. This method comprises administering to a human in need of supplemental fatty acids a fatty acid composition that is readily dispersed in liquid by stirring or shaking. The fatty acid composition is the composition described above. The method can comprise providing the fatty acid composition in powder form which is substantially free of triglycerides, and then adding the fatty acid composition powder to a liquid and stirring or shaking the liquid with the fatty acid composition to form a stable dispersion. In accordance with an aspect of the method and wherein human is an infant, toddler, child, adolescent or adult, the liquid can be a milk or milk substitute. In the instance in which the human is an infant or toddler, the milk substitute can be infant, toddler, or pediatric formula. In accordance with another aspect of this method, the fatty acid composition can be provided as a powder, and the fatty acid composition powder can be added to a liquid along with a milk powder or a milk substitute powder. In this instance the liquid is preferably water. The milk powder can be skim milk powder and/or whole milk powder. The milk substitute powder can, for example, be infant, toddler, or pediatric formula powder.

In accordance with a further aspect of the invention, a method of fortifying a milk or milk substitute with a fatty acid component is provided which comprises combining a fatty acid composition as described above with a milk or milk substitute and dispersing the fatty acid composition in a liquid by stirring or shaking. The milk or milk substitute can be provided as liquid or as powder. If the milk or milk substitute is provided as powder, then the liquid is water, and the method comprises adding the milk powder or milk substitute powder and the fatty acid composition powder to the water, and stirring or shaking the powders in the water to form a dispersion. The milk/milk substitute powder and the fatty acid composition powder can be added to the liquid simultaneously. In this instance, the powders can be combined together prior to adding the powders to the liquid.

In accordance with a further aspect of the invention, a fatty acid supplement is provided which can be quickly and easily dispersed in a liquid. The fatty acid supplement comprises a fatty acid component which dissociates in a human stomach upon consumption by a human and which is present in a fatty acid composition which forms a stable dispersion in the liquid. The fatty acid supplement is substantially free of triglycerides. The fatty acid composition is the fatty acid composition as described above.

In accordance with a further aspect of the invention, a method of providing a human with supplemental fatty acids is disclosed. The method comprises administering to a human in need of supplemental fatty acids a dispersion containing a fatty acid composition which is substantially free of triglycerides, the fatty acid composition comprising a fatty acid component which dissociates in the human stomach to be readily available for absorption by the human digestive tract. The fatty acid composition is the fatty acid composition as described above.

DETAILED DESCRIPTION OF THE INVENTION

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description. The claimed invention is capable of other embodiments and of being practiced or being carried out in various ways. Also, it is to be understood that the phraseology and terminology used herein is for the purpose of description and should not be regarded as limiting.

We have developed a fatty acid composition which readily disperses in liquids, such as water, formula, milk, milk products and milk-like products (such as milk substitutes))

to form a stable dispersion without the need for traditional microencapsulation of the fatty acids. The composition is a mixture of free-flowing salts of fatty acids (e.g., omega-3 or omega-6 fatty acids) that rapidly disperses in an aqueous medium and is able to be reconstituted in milk or a milk-based food composition. The dried powder forms a stable dispersion in the liquids.

The terms "nutritional product" or "nutritional composition" or "nutritional formulation" are used interchangeably and refer to liquid and solid, including semi-liquid and semi-solid. Examples of semi-liquids are gels, oil-in-water emulsions, and shakes. Examples of semi-solids are creams, gelatins, and doughs. The solids may be powders that may be reconstituted to form a nutritional liquid which is suitable for human consumption.

The term "nutritional powder" as used herein, unless otherwise stated, refers to nutritional products in free-flowing or scoopable form that can be reconstituted with water, milk, milk-like liquids, or other liquids prior to consumption. This includes both spray-dried, dry mixed, and dry blended powders.

The term "nutritional liquid" as used herein, unless otherwise stated, refers to nutritional products in ready-to-feed liquid form, concentrated form, and nutritional liquids made by reconstituting the powder disclosed herein prior to use.

The term "fatty acid component" as used herein, unless otherwise stated, refers to free fatty acids or fatty acid salts.

Product Form

The fatty acid-containing nutritional product and associated methods disclosed herein may be formulated and administered in any known or suitable oral form.

The fatty acid composition can be formulated as a powder, and can be provided to consumers as a powder which can then be added to a liquid. Alternatively, the powder can be provided to manufacturers who then add the powder to formula, milk, milk products and milk-like products (including milk substitutes) to provide a fatty acid fortified liquid product. The fatty acid composition can, alternatively, be combined, for example, with milk powder, to produce a fatty acid fortified milk powder. This fatty acid fortified milk powder would then be mixed with water to form a fatty acid fortified milk beverage. The nutritional product (i.e., the powdered fatty acid composition or a commercial food or beverage which includes the fatty acid composition) is commercially stable after being packaged and then stored at 20-25° C. for at least 3 months, including 6 to 24 months, and including 12 to 18 months. Accelerated stability (i.e., shelf life) studies show that the fatty acid composition will be stable for 36 months and even as long as 48 months.

In one embodiment, the fatty acid composition comprises a desired fatty acid component combined with vitamins, inorganic salts, protein and carbohydrates. In another embodiment, the fatty acid composition includes the fatty acid component combined with vitamins and inorganic salts. This embodiment does not include protein or carbohydrates. Hence, the protein and carbohydrates can be considered optional components to the fatty acid composition, and either or both of these components can be omitted from the fatty acid composition. In a further embodiment, the fatty acid composition comprises only a spray dried fatty acid salt (i.e., excludes vitamin, inorganic salt, protein and carbohydrate).

Preferred fatty acids are ARA, DHA and any omega-3 or omega-6 fatty acid either individually or in combinations. The omega-3 rich fatty acid can be chosen from the group consisting of predominantly alpha-linolenic acid (C18:3, n-3), eicosatetraenoic acid (C20:4, n-3), moroctic acid (C18: 4, n-3), eicosapentaenoic acid (EPA) (C20:5, n-3), heneicosapentaenoic acid (C21:5, n-3), docosapentaenoic acid (C22:5, n-3), and docosahexaenoic acid (DHA) (C22:6, n-3), and combinations thereof. The omega-6 fatty acid can be chosen from the group consisting of linoleic acid 18:2 (n-6), eicosatrienoic acid 20:3 (n-6), arachidonic acid 20:4 (n-6), and combinations thereof. In one embodiment, the fatty acid component selected is a long-chain polyunsaturated fatty acid (LCPUFA's) of 18-carbon chains or longer containing at least two, and preferably at least four, double bonds.

The fatty acid(s) come from a source (e.g., fungal oil, algal oil, or fish oil) which comprises a complex mixture of fatty acids rich in ARA, EPA, DHA, omega-3 fatty acids, and/or omega-6 fatty acids. The fatty acid source is not exclusively composed of one acid; that is, the fatty acid source is not, for example, pure DHA, but is rather a complex mix of different fatty acids. Another source of fatty acid can be a fungal oil, such as is produced by a species of *Mortierella*, and in particular such as is produced by *M. alpina*. *M. alpina* advantageously produce ARA in a concentration amount practical for incorporation into infant formula with an ARA concentration similar to that in human breast milk. Thus, a fatty acid component wherein the fatty acid source is *M. alpina* can be used to produce ARA-salt fortified infant formula. Additional suitable sources of fatty acids include corn oil, coconut oil, high oleic sunflower oil, soybean oil, medium chain triglycerides (MCT) oil, safflower oil, high oleic safflower oil, palm oil, palm kernel oil, olive oil, oleic acids, canola oil, and mixtures and combinations thereof Composition Examples In accordance with one aspect of the invention, the dried fatty acid composition comprises a mixture of free fatty acid salts (derived as described above) that may be formulated in combination with inorganic salts, vitamins, and optionally a protein and carbohydrates. The inorganic salt can be a sodium or a potassium citrate or a sodium or a potassium phosphate.

Vitamins:

The vitamins in the fatty acid composition can include suitable sources, for example, of vitamin C, vitamin A, vitamin E, vitamin D, vitamin K, vitamin B12, choline, folic acid, thiamine, riboflavin, carotenoids, niacin, pantothenic acid, biotin, mixed isomers of tocopherol, salts and derivatives of the noted vitamins, and combinations thereof. Other vitamins can be included as well if desired. To provide a shelf-stable fatty acid composition, low levels of both vitamin C and vitamin E derivatives may be required. The reasonable expectation is that a maximum of about 3% ascorbate salt will be needed, and that tocopherols will be required in levels of less than 1%.

Protein:

The fatty acid composition or fatty acid fortified nutritional product may optionally comprise protein. Examples of suitable protein sources include skim milk powder, whole milk powder, nonfat milk powder, casein, caseinates (such as sodium, potassium or calcium caseinate), soy, pea, and whey protein. Proteins such as casein and whey have emulsifying properties and are also able to inhibit lipid oxidation by scavenging free radical intermediates and chelating pro-oxidant metals thus increasing oxidative stability. Both proteins are generally regarded as safe (GRAS).

Carbohydrates:

The fatty acid composition may optionally comprise a carbohydrate source. Any carbohydrate source that is suitable for use in nutritional products and is compatible with the elements of such products is suitable for use in combination with the fatty acid component. Non-limiting examples of suitable carbohydrate sources, if used, include maltodextrin, sugar, modified sugar, modified starch or cornstarch, glucose, corn syrup or solids, rice-derived carbohydrates, bran-derived carbohydrates, various vegetable-derived carbohydrates, sugar alcohols, artificial sweeteners, and combinations thereof.

Inorganic Salts:

The inorganic salts of the composition can include citric acid and its salts and derivatives and phosphate sources such as dibasic sodium phosphate, tetrasodium diphosphate, tricalcium phosphate, dibasic potassium phosphate, tetrapotassium diphosphate, ammonium phosphate salt, and combinations thereof. Other inorganic salts could be used as well.

Other Optional Ingredients

The fatty acid composition may optionally comprise other ingredients in addition to the fatty acid component. Such optional ingredients may modify the physical, chemical, aesthetic, or processing properties of the composition. Such ingredients are known or suitable for use in nutritional products and may be used in the fatty acid composition described herein. Such ingredients are safe for oral consumption and are compatible with the ingredients of the nutritional product. Non-limiting examples of such optional ingredients, if used, include preservatives, anti-oxidants, emulsifying agents, flow agents, buffers, flavoring, thickening agents, additional nutrients and combinations thereof. The preservatives can, for example, include butylated hydroxytoluene (BHT). The anti-oxidants can, for example, include ascorbyl palmitate. The emulsifying agents can, for example, include soy lecithin. The flow agents can, for example, include tricalcium phosphate or silicates. The buffers can, for example, include calcium carbonate.

A preferred composition of the fatty acid powder comprises a sodium (Na) salt of the fatty acid, an inorganic salt, vitamins, a protein source, and a carbohydrate source. As an alternative, a potassium (K) salt of the fatty acid can used instead of (or in combination with) a sodium (Na) fatty acid component. The inorganic salt can be a phosphate. If a mixture of sodium and potassium salts of the fatty acid is used, then the phosphate may be a combination of sodium, calcium and potassium phosphates. The free fatty acid component could include other monovalent cations, such as sodium, potassium, ammonium and the free base forms of choline, lecithin, alanine, arginine, asparagine, aspartic acid, cysteine, glutamic acid, glutamine, glycine, ornithine, proline, selenocysteine, serine, tyrosine, histidine, isoleucine, leucine, lysine, methionine, phenylalanine, threonine, tryptophan, valine, and combinations thereof. However, regardless of the monovalent cation of the fatty acid component, the phosphate salts will be potassium, sodium, calcium, and/or ammonium phosphates or combinations thereof.

The concentration of the fatty acid component present in the final powder product varies based on the concentration of a particular fatty acid in the starting triglyceride oil. Commercially available triglyceride oils vary from about 30% "EPA+DHA" content to higher than 90% pure EPA or DHA, which can also be in triglyceride form.

Table I below shows the percentage by weight of the various compounds in the powder composition.

TABLE I

| Compound | Function/Purpose | % by weight of dried powder |
|---|---|---|
| Fatty acid component | Source of fatty acid for supplementation | about 10% to about 100% by weight, preferably about 50% to about 90%, and preferably about 65% to about 75% by weight or preferably about 90% to about 100% by weight |
| Phosphate source | inorganic salt, Buffer, flow modifier, improves color | 0% to about 50% by weight, preferably about 2% to about 30%, and preferably about 10% |
| Sodium citrate | inorganic salt, Sequestering agent, buffer | about 0% to about 3%, and preferably about 1% |
| Sodium ascorbate | Vitamin, Anti-oxidant | about 0% to about 4%, preferably about 2% to about 4%, and preferably about 1% |
| Maltodextrin, sugar or starch derivatives, rice or bran derivative | Source of carbohydrates, improves color, texture and flow properties | 0% to about 70%, preferably, about 0% to about 5%, and preferably about 5% |
| Skim milk powder, whole milk powder, sodium or calcium caseinate/whey protein | Source protein, also acts as emulsifier, wetting, dispersing, and instantizing agent | 0% to about 40%, and preferably about 20% |

Methods of Manufacture

The fatty acid component or composition may be prepared by any known or otherwise effective manufacturing technique. The fatty acid component or composition can be prepared by one skilled in the art based on the disclosed information herein. The fatty acid component can also be purchased (or otherwise prepared elsewhere).

The method of preparing the fatty acid component initially comprises saponification of a triglyceride or of an ester to form the free fatty acid. The free fatty acid can then be converted to a fatty acid salt.

Saponification Followed by Conversion

Saponification of a triglyceride or of an ester to the free fatty acid is carried out in a manner well known in the field. The manner of performing the saponification thus need not be described.

Conversion of the Free Fatty Acid into the Corresponding Fatty Acid Salt

In one method, the fatty acid component may be prepared by converting the free fatty acid to the corresponding salt with an alkaline metal hydroxide under an inert atmosphere. The resulting emulsion is then spray dried to yield the fatty acid component as a powder. Examples of suitable alkaline metal hydroxides include sodium hydroxide or potassium hydroxide.

In another method, the free fatty acid can be converted to a fatty acid salt using an alkaline metal hydroxide. The fatty acid salt may be mixed with the ingredients described herein to form the fatty acid composition. The fatty acid composition can be dried or placed into an aqueous suspension for spray drying.

The disclosed methods can be performed under an inert atmosphere, e.g., under nitrogen or argon.

The source of fatty acids and alkaline metal hydroxide can be mixed by any method known in the art, and can be accomplished mechanically or manually, and using any desired mixing equipment or technology.

Mixing can be performed at various temperatures. The temperature is dependent upon the particular source of fatty acid, the identity of the alkaline metal hydroxide, and other factors, e.g. the amounts of the raw materials being used. Non-limiting examples of suitable temperatures include from about 10° C. to about 100° C., from about 15° C. to about 100° C., and from about 20° C. to about 80° C. Pre-heating of the reaction mixture may be performed at any of the temperature ranges disclosed herein. Heating and/or pre-heating can occur over a period of time from about 10 minutes to about 90 minutes.

The powdered fatty acid composition can be formed via a spray drying process or by a dry mixing process. Such processes and the equipment for carrying out such processes are well known, and need not be described herein.

In accordance with one aspect of the spray-drying method, an aqueous slurry or liquid comprising the fatty acid component, and protein, carbohydrates, inorganic salts (which can optionally include a phosphate salt), and vitamins is prepared. This slurry/liquid is then spray dried to produce a spray dried powder. As noted above, the powder can be formed without the protein or carbohydrates. It has been observed that in compositions including caseinates, that the caseinate salt preferentially reside at the surface of the fatty acid salts, such that the caseinate surrounds the fatty acid salt component. This migration of the caseinate relative to the fatty acid salt has been termed in-situ microencapsulation or substance segregation. Having the caseinate salt at the surface of the composition particles is believed to help with the flowability and stability of the fatty acid composition powder. It is expected that other compounds such as soy protein isolate, pea protein isolate, and hydrolyzed protein may also enhance flowability and stability. Although this results in an in-situ microencapsulation of the fatty acid component, this in-situ microencapsulation is to be distinguished from the intentional or traditional microencapsulation of the triglycerides, as discussed in the Background Section. Because of this, our powder is deemed to not be microencapsulated.

When traditionally microencapsulated PUFAs (as discussed above in the Background) are compared to our fatty acid composition, several desirable advantages favor our fatty acid composition. The fatty acid composition is instantizable (i.e., it quickly and easily disperses in liquid) and generates a stable dispersion with little or no load issue. The fatty acid component has a similar fatty acid profile to the microencapsulated PUFAs. Because of these attributes, the fatty acid composition may provide superior performance for oxidative degradation, odor, taste and stability in many formulations.

Composition Examples

Tables IIA-IIE below summarize the weight percentages of the components for 17 different fatty acid compositions.

TABLE IIA

| Ingredients, % Weight | Example 1 | Example 2 | Example 3 | Example 4 |
|---|---|---|---|---|
| Total Sodium Fatty Acid Mixture | 56.20 | 70.00 | 65.97 | 65.97 |
| Sodium ARA | (26) | (32.00) | | |
| Sodium DHA | | | (26.00) | (26.00) |
| Sodium phosphate | 2.40 | 20.00 | 5.00 | 5.00 |

TABLE IIA-continued

| Ingredients, % Weight | Example 1 | Example 2 | Example 3 | Example 4 |
|---|---|---|---|---|
| Sodium caseinate | 38.40 | | 25.00 | |
| Nonfat Instant dry milk | | | | 25.00 |
| Sodium ascorbate | 2.90 | 3.00 | 1.00 | 1.00 |
| Maltodextrin | | 5.00 | 2.00 | 2.00 |
| Sodium citrate | | 2.00 | 1.00 | 1.00 |
| Antioxidant | | | 0.03 | 0.03 |
| ARA:Phosphate Ratio | | 1.6:1 | | |
| DHA:Phosphate Ratio | | | 5.2:1 | 5.2:1 |
| Wt % ARA/DHA of dried powder composition | 24 | 29 | 24 | 24 |

TABLE IIB

| Ingredients, % Weight | Example 5 | Example 6 |
|---|---|---|
| Total Sodium Fatty Acid Mixture | 65.00 | 63.47 |
| Potassium ARA | (29.00) | (29.00) |
| Sodium phosphate | 8.00 | |
| Potassium phosphate | | 8.50 |
| Calcium phosphate | 0.97 | 1.00 |
| Sodium caseinate | 19.00 | 20.00 |
| Sodium ascorbate | 1.00 | 1.00 |
| Maltodextrin | 5.00 | 5.00 |
| Sodium citrate | 1.00 | 1.00 |
| Antioxidant | 0.03 | 0.03 |
| DHA:Phosphate Ratio | 3.8:1 | 3.3:1 |
| Wt % DHA of dried powder composition | 26 | 25 |

TABLE IIC

| Ingredients, % Weight | Example 7 | Example 8 | Example 9 | Example 10 |
|---|---|---|---|---|
| Total Sodium Fatty Acid Mixture | 63.97 | 76.00 | 75.00 | 70.00 |
| Sodium ARA | (29.00) | (35.00) | (34.00) | |
| Sodium DHA | | | | (28.00) |
| Sodium phosphate | 8.00 | 20.00 | 20.00 | 25.00 |
| Calcium phosphate | 1.00 | | | |
| Sodium caseinate | 20.00 | | | |
| Sodium ascorbate | 1.00 | 4.00 | 3.00 | 3.00 |
| Maltodextrin | 5.00 | | | |
| Sodium citrate | 1.00 | | 2.00 | 2.00 |
| Antioxidant | 0.03 | | | |
| ARA:Phosphate Ratio | 3.6:1 | 1.7:1 | 1.7:1 | |
| DHA:Phosphate Ratio | | | | 1.1:1 |
| Wt % ARA/DHA of dried powder composition | 27 | 33 | 32 | 26 |

The fatty acid compositions of Examples 1-7 were all relatively free flowing when dry. When mixed with milk, they dispersed quickly (i.e., in a matter of seconds) by stirring or shaking. Any other desired method of agitating the powder in the liquid such that the powder disperse in the liquid could have been used as well. The milk/powder mixture remained dispersed for at least several hours (at which point monitoring ceased). Thus, the fortified liquid drink formed with the powder compositions were all considered to be highly stable; that is, the composition remained dispersed in the liquid. Composition Examples 8-10 differ from Examples 1 and 3-7 in that they exclude protein and carbohydrates. They too dispersed quickly in liquid and remained dispersed in the liquid for extended periods of time. Hence, the compositions of Examples 8-10 are also deemed to be stable.

TABLE IID

| Ingredients, % Weight | Example 11 | Example 12 | Example 13 |
|---|---|---|---|
| Total Sodium Fatty Acid Mixture | 89.00 | 85.00 | 75.70 |
| Sodium ARA | (40.00) | (38.00) | (34.00) |
| Sodium phosphate | 6.00 | 10.00 | 20.00 |
| Rice bran extract | 1.00 | 1.00 | 0.80 |
| Sodium ascorbate | 4.00 | 4.00 | 3.50 |
| ARA:Phosphate Ratio | 6.9:1 | 3.7:1 | 1.7:1 |
| Wt % ARA of dried powder composition | 37 | 35 | 31 |

TABLE IIE

| Ingredients, % Weight | Example 14 | Example 15 | Example 16 | Example 17 |
|---|---|---|---|---|
| Total Sodium Fatty Acid Mixture | 70.00 | 65.97 | 74.50 | 85.00 |
| Sodium ARA | (31.00) | | | (38.00) |
| Sodium DHA | | (28.00) | (32.00) | |
| Sodium phosphate | 20.00 | 30.00 | 20.00 | 6.00 |
| Rice bran extract | | | | 5.00 |
| Sodium ascorbate | 3.40 | 1.00 | 3.50 | 4.00 |
| Maltodextrin | 5.00 | 2.00 | | |
| Sodium citrate | 1.60 | 1.00 | 2.00 | |
| Antioxidant | | 0.03 | | |
| ARA:Phosphate Ratio | 1.5:1 | | | 0.29 |
| DHA:Phosphate Ratio | | 0.9:1 | 1.6:1 | |
| Wt % ARA/DHA of dried powder composition | 29 | 27 | 30 | 36 |

Examples 11, 12, 13 and 17 demonstrate that the use of rice bran can improve dissolution rates. Examples 11-14 and 16-17 use higher sodium ascorbate levels and can be expected to have greater stability than the other compositions.

Fatty Acid Component Only Composition Examples

Two examples were also prepared that, as shown in Table IIF below, comprised only spray dried fatty acid component. That is, the compositions were 100% fatty acid salt, and had no proteins, vitamins, carbohydrates, or inorganic salts mixed with the fatty acid component. The powder form of the fatty acid composition was formed by spray drying the fatty acid composition.

TABLE IIF

| Ingredients | Composition Example 18 (ARA) | | Composition Example 19 (DHA) | |
|---|---|---|---|---|
| | Quantity (grams) | Percent of Formulation | Quantity (grams) | Percent of Formulation |
| Total Sodium fatty acid mixture | 10.7 | 100 | 10.8 | 100 |
| Sodium ARA content in the sodium gatty acid mixture | 4.83 | 45 | | |
| Sodium DHA content in the sodium fatty acid mixture | | | 4.24 | 39 |
| Wt % ARA/DHA of dried powder composition | | 42 | | 37 |

From Examples 18 and 19, we determined that spray dried fatty acid compositions comprised only of Na-ARA, Na-DHA, K-ARA, or K-DHA dispersed quickly and easily in liquids.

In examples 1-19 above, the fatty acid composition for each example was not microencapsulated. That is, although some of the compositions may have exhibited in-situ microencapsulation, none of the compositions were exposed to a microencapsulation step which would encapsulate the composition in a waxy or carbohydrate substrate, as occurs with traditional (intentional) microencapsulation.

Table III below tabulates the percentages of the various ingredients of the powder compositions when broadly categorized. As noted above, currently available microencapsulated fatty acid supplements contain only 10-15 wgt % PUFA. As seen from Table III below, our fatty acid composition contains a range of about 24 wgt % to about 42 wgt % of the desired fatty acid. This represents a substantial increase in available fatty acid relative to currently available products. This increase in the weight percent of fatty acid in the powder means that less of our powder is needed to deliver the same amount of fatty acid than if the currently available 10-15 (wgt) % PUFA product is used.

For example, assuming that an infant formula manufacturer preparing a batch of infant formula by dry mixing, specifies the addition of 100 kg of the currently available "Cargill 15% ARA Powder", the same manufacturer, choosing to use the our "37% ARA-Sodium Composition" (Example No. 11, above) would need to add only about 40 kg, representing approximately a 60% reduction in the amount of fatty acid composition needed to achieve the same loading. An additional benefit is that, because of the higher concentration of ARA or DHA in our formulation, there are much lower levels of other excipients in the formulation. This simplifies the formulator's task of formulating a sole nutritional source product, like an infant formula, and clearly increases the flexibility of defining the formulation.

TABLE III

| Composition Example | Desired Fatty Acid | Total % Na/K fatty acid | % desired Na/K fatty acid | desired fatty acid % of dried powder | % Inorganic Salt (including any phosphate) | Desired fatty acid/ phosphate ratio | % Protein | % Vitamins* | % Carbohydrates |
|---|---|---|---|---|---|---|---|---|---|
| 1 | ARA | 56 | 26 | 25 | 2.4 | 10.4:1 | 38 | 2.9 | 0 |
| 2 | ARA | 70 | 32 | 29 | 22 | 1.6:1 | 0 | 3 | 5 |
| 3 | DHA | 66 | 26 | 24 | 6 | 5.2:1 | 25 | 1 | 2 |
| 4 | DHA | 66 | 26 | 24 | 6 | 5.2:1 | 25 | 1 | 2 |
| 5 | ARA | 65 | 29 | 26 | 9 | 3.8:1 | 19 | 1 | 5 |

TABLE III-continued

| Composition Example | Desired Fatty Acid | Total % Na/K fatty acid | % desired Na/K fatty acid | desired fatty acid % of dried powder | % Inorganic Salt (including any phosphate) | Desired fatty acid/ phosphate ratio | % Protein | % Vitamins* | % Carbohydrates |
|---|---|---|---|---|---|---|---|---|---|
| 6 | ARA | 63 | 29 | 25 | 10.5 | 3.3:1 | 20 | 1 | 5 |
| 7 | ARA | 64 | 29 | 27 | 10 | 3.6:1 | 20 | 1 | 5 |
| 8 | ARA | 76 | 35 | 33 | 20.7 | 1.7:1 | 0 | 4 | 0 |
| 9 | ARA | 75 | 34 | 32 | 22 | 1.7:1 | 0 | 3 | 0 |
| 10 | DHA | 70 | 28 | 26 | 27 | 1.1:1 | 0 | 3 | 0 |
| 11 | ARA | 89 | 40 | 37 | 5.8 | 6.9:1 | 0 | 4 | 1 |
| 12 | ARA | 85 | 38 | 35 | 10 | 3.7:1 | 0 | 4 | 1 |
| 13 | ARA | 76 | 34 | 31 | 20 | 1.7:1 | 0 | 3.5 | 0.8 |
| 14 | ARA | 70 | 31 | 29 | 22.1 | 1.5:1 | 0 | 3.4 | 5 |
| 15 | DHA | 66 | 28 | 27 | 31 | 0.9:1 | 0 | 1 | 2 |
| 16 | DHA | 75 | 32 | 30 | 22 | 1.6:1 | 0 | 3.5 | 0 |
| 17 | ARA | 85 | 38 | 36 | 5.5 | 7:1 | 0 | 4 | 5 |
| 18 | ARA | 100 | 45 | 42 | 0 | — | 0 | 0 | 0 |
| 19 | DHA | 100 | 39 | 37 | 0 | — | 0 | 0 | 0 |
| Range (wt %) | | 56-89 | 26-40 | 24-42 | 2.4-31 | 0.9:1-10.4:1 | 0-38 | 1-4 | 0-5 |

*The vitamins in the examples included sodium ascorbate is "vitamin".
The percentages reflect the correction for the Na-content of the sodium ascorbate (by multiplying by 0.89).

TABLE IVA

| Ingredient | Function | Powder Example 1 (ARA) | Powder Example 2 (ARA) | Powder Example 3 (DHA) | Powder Example 4 (DHA) | Powder Example 5 (DHA) |
|---|---|---|---|---|---|---|
| % Na/K fatty acid | Fatty acid mixture | 56.2 | 70 | 66 | 66 | 65 |
| % desired Na/K fatty acid | Fatty acid | 26 | 32 | 26 | 26 | 29 |
| % Na/K/Ca Phosphate source | Inorganic salt, Buffer, flow modifier, improves color | 2.4 | 20 | 5 | 5 | 9 |
| % Skim, whole, nonfat milk powders, caseinates (such as sodium or calcium), whey protein | Protein, Emulsifier, wetting, dispersing, and instantizing agent | 38 | | 25 | 25 | 19 |
| % Maltodextrin, sugar/sugar derivatives | Carbohydrate, improves color, texture, and flow | | 5 | 2 | 2 | 5 |
| % Na-ascorbate | Vitamin, antioxidant | 3 | 3 | 1 | 1 | 1 |
| % Na-citrate | Inorganic salt, sequestering agent, buffer | | 2 | 1 | 1 | 1 |

TABLE IVB

| Ingredient | Function | Powder Example 6 (ARA) | Powder Example 7 (ARA) | Powder Example 8 (ARA) | Powder Example 9 (ARA) | Powder Example 10 (DHA) |
|---|---|---|---|---|---|---|
| % Na/K fatty acid | Fatty acid mixture | 63.5 | 64 | 76 | 75 | 70 |
| % desired Na/K fatty acid | Fatty acid | 29 | 29 | 35 | 34 | 28 |
| % Na/K/Ca phosphate source | Inorganic, Salt, Buffer, flow modifier, improves color | 9.5 | 9 | 20 | 20 | 25 |

TABLE IVB-continued

| Ingredient | Function | Powder Example 6 (ARA) | Powder Example 7 (ARA) | Powder Example 8 (ARA) | Powder Example 9 (ARA) | Powder Example 10 (DHA) |
|---|---|---|---|---|---|---|
| % Skim, whole, nonfat milk powders, caseinates (such as sodium or calcium), whey protein | Protein, Emulsifier, wetting, dispersing, and instantizing agent | 20 | 20 | | | |
| % Maltodextrin, sugar, and sugar derivatives | Carbohydrate, improves color, texture, and flow | 5 | 5 | | | |
| % Na-ascorbate | Vitamin, antioxidant | 1 | 1 | 4 | 3 | 3 |
| % Na-citrate | Inorganic Salt, sequestering agent, buffer | 1 | 1 | | 2 | 2 |

TABLE IVC

| Ingredient | Function | Powder Example 11 (ARA) | Powder Example 12 (ARA) | Powder Example 13 (ARA) | Powder Example 14 (ARA) | Powder Example 15 (DHA) |
|---|---|---|---|---|---|---|
| % Na/K fatty acid | Fatty acid mixture | 89 | 85 | 75.7 | 70 | 66 |
| % desired Na/K fatty acid | Fatty acid | 40 | 38 | 34 | 31 | 28 |
| % Na/K/Ca phosphate source | Inorganic Salt, Buffer, flow modifier, improves color | 6 | 10 | 20 | 20 | 30 |
| % Skim, whole, nonfat milk powders, caseinates (such as sodium or calcium), whey protein | Protein, Emulsifier, wetting, dispersing, and instantizing agent | | | | | |
| % Maltodextrin, sugar, and sugar derivatives | Carbohydrate, improves color, texture, and flow | | | | 5 | 2 |
| Lecithin, rice bran extract | Carbohydrate, Emulsifier, wetting, dispersing, and instantizing agent | 1 | 1 | 0.8 | | |
| % Na-ascorbate | Vitamin, Antioxidant | 4 | 4 | 3.5 | 3.4 | 1 |
| % Na-citrate | Inorganic Salt, sequestering agent, buffer | | | | 1.6 | 1 |

TABLE IVD

| Ingredient | Function | Powder Example 16 (DHA) | Powder Example 17 (ARA) | Powder Example 18 (ARA) | Powder Example 19 (DHA) | Range (wt %) (exclusive of Examples 18 & 19) |
|---|---|---|---|---|---|---|
| % Na/K fatty acid | Fatty acid mixture | 74.5 | 85 | 100 | 100 | 63.5-89 |
| % desired Na/K fatty acid | Fatty acid | 32 | 38 | 45 | 39 | 26-40 |
| % Na/K/Ca phosphate source | Inorganic Salt, Buffer, flow modifier, improves color | 20 | 6 | | | 2.4-30 |

TABLE IVD-continued

| Ingredient | Function | Powder Example 16 (DHA) | Powder Example 17 (ARA) | Powder Example 18 (ARA) | Powder Example 19 (DHA) | Range (wt %) (exclusive of Examples 18 & 19) |
|---|---|---|---|---|---|---|
| % Skim, whole, nonfat milk powders, caseinates (such as sodium or calcium), whey protein | Protein, wetting, dispersing, and instantizing agent | | | | | 0-38 |
| % Maltodextrin, sugar, and sugar derivatives | Carbohydrate, improves color, texture, and flow | | | | | 0-5 |
| Lecithin, rice bran extract | Carbohydrate, Emulsifier, wetting, dispersing, and instantizing agent | | 5 | | | 0-5 |
| % Na-ascorbate | Vitamin, antioxidant | 3.5 | 4 | | | 1-4 |
| % Na-citrate | Inorganic Salt, sequestering agent, buffer | 2 | | | | 0-2 |

Examples of Fortified Nutritional Drink Products with a Fatty Acid Composition:

Test solutions of fatty acid compositions were prepared for taste and organoleptic evaluations. These test sample solutions comprise reconstituted milk solids in water as the medium, along with a fatty acid composition. Test solutions were evaluated against a blank which did not contain the fatty acid composition.

The milk fat concentration may be in the range of 12 g/L (about 1% milk fat) to 26 g/L (about 2.5% milk fat), with a target of about 24 g/L (about 2.4% milk fat). The precise fat content of an infant formula drink, along with the precise fatty acid contents are strictly regulated by national food standards codes. The desired fat concentrations were achieved using a blend of whole milk powder (WMP) and skim milk powder (SMP).

Examples of fatty acid fortified infant formula were prepared by adding the milk powder blend and the fatty acid composition to water using the compositions from Example Numbers 8, 13, 14, and 16 above. The slurry of solids was shaken vigorously by hand until dispersed. Dissolution time was typically in the range of 45 seconds. The formulated Na-ARA and Na-DHA powders employed in the following Drink Preparation Examples 1 and 2 below, were completely dispersed after the "vigorous shaking" step without exception.

In the preparation of the "DHA Fortified Breakfast Drink" described below in "Drink Example 3", cold skim milk was added to the dry breakfast drink powder and the sodium DHA composition as recommended by the manufacturer.

Drink Preparation Example 1:

Infant Formula Fortified With ARA and DHA, in ratios specified by Food Safety Guidelines:

Preparation of Fatty Acid Fortified Milk with a Na-DHA Composition with and without a Na-ARA Component in the Same Solution

| Test Solution Name: Sample Name: | A: DHA Only "Na-DHA Composition": | B: DHA + ARA "Na-ARA Component": | Blank |
|---|---|---|---|
| DHA or ARA, % weight, calc'd | 30.1 | 28.6 | 0.0 |
| Taste Test Solution Volume: | 250-mL | 250-mL | 250-mL |
| Target Weight Fat: | 5.91 | 5.91 | 5.91 |
| Target Weight DHA: | 0.0296 | 0.0296 | 0.00 |
| Target Weight ARA: | 0.0000 | 0.0591 | 0.0 |
| (weights to use in bold italics below) | | | |
| "Na-DHA Composition": 30.1% DHA Component (Powder Example 16) | *0.0982* | *0.0982* | |
| "Na-ARA Composition" 28.6% ARA Component (Powder Example 14) | | *0.207* | |
| Blank | | | No ARA |
| WMP | *19.70* | *19.70* | *19.70* |
| SMP | *13.55* | *13.55* | *13.55* |
| Water | *216.7* | *216.5* | *216.8* |

| Milk Powder Compositions: | % Fat: |
|---|---|
| Whole Milk Powder (WMP) | 30.0 |
| Skimmed Milk Powder (SMP) | 0.0 |

Drink Preparation Example 2:

An Example of a Potential Infant Formula Fortification With ARA Only:

Preparation of Fatty Acid Fortified Milk with a Sodium ARA Composition with and without an Emulsifier

| Test Solution Name: | Test Solution A | Test Sol. B | Blank |
|---|---|---|---|
| Sample Name: | "Na ARA Composition with Emulsifier": | "Na ARA Component w/o Emulsifier": | |
| ARA, % weight calc'd | 31.1 | 31.4 | 0.0 |
| Emulsifier (Rice bran) Conc., wt. %: | 0.8 | 0.0 | 0.0 |
| Taste Test Solution Volume: | 250-mL | 250-mL | 250-mL |
| Target Weight Fat: | 6.56 | 6.56 | 6.56 |
| Target Weight ARA: | 0.0656 | 0.0656 | 0.0 |
| (weights to use in bold italics below) | | | |
| "Na ARA Composition with Emulsifier": | | | |
| 31.1% ARA Powder (Powder Example 13) | *0.211* | | |
| "Na ARA Composition w/o Emulsifier.": | | | |
| 31.4% ARA Powder (Powder Example 8) | | *0.209* | |
| Blank | | | No ARA |
| WMP | *21.88* | *21.88* | *21.88* |
| SMP | *11.38* | *11.38* | *11.38* |
| Water | *216.5* | *216.5* | *216.8* |
| Milk Powder Compositions: | | % Fat: | |
| Whole Milk Powder (WMP) | | 30.0 | |
| Skimmed Milk Powder (SMP) | | 0.0 | |

Drink Example 3:

Breakfast Drink Fortified With DHA, Aimed at Delivering 25% of the recommended daily allowance (RDA) for DHA as determined by the Global Organization for EPA and DHA omega-3s (GOED).

Preparation of a Skim Milk Based Vanilla Breakfast Drink Fortified with a Na-DHA Composition to Provide 25% of RDA for DHA

| Test Solution Name: | "DHA Fortified Breakfast Drink" |
|---|---|
| Sample Name: | "Na-DHA Fortified Breakfast Drink Powder": |
| DHA, % weight calc'd | 30.1 |
| Taste Test Solution Weight, g: | 285 |
| Target Weight DHA: | 0.0625 |
| (to provide 25% RDA) | |
| (weights to use in bold italics below) | |
| "Na-DHA Composition": | |
| 30.1% DHA Powder | *0.208* |
| Weight Vanilla Drink Mix Powder, g: (1-metallized packet) | *36* |
| Volume Cold Fat-free Milk, 1-cup: | *240-mL* |
| Weight 1-cup Fat-free Milk, g: | *249* |

Mixing Instructions for breakfast, from bag label:

(1) Empty "vanilla drink mix powder" packet into a large glass.

(2) Add the specified amount of "Na-DHA Composition" to the powder in the glass.

(3) Add 1 cup cold fat-free milk.

(4) Stir to dissolve until consistent.

The Tables below put in table form fortified liquids made by mixing selected compositions in water.

Preparation of Fatty Acid Fortified Milk with Na-DHA Composition with and without a Na-ARA Component

| Ingredient | Example 8 | Example 13 | Blank 1 | Example 14 | Example 16 | Blank 2 |
|---|---|---|---|---|---|---|
| Na-DHA Composition, % Weight | 0.00 | 0.00 | 0.00 | 30.10 | 30.10 | 0.00 |
| Na-ARA Composition, % Weight | 31.40 | 31.10 | 0.00 | 28.60 | 0.00 | 0.00 |
| DHA, Fatty Acid Composition, (g) | 0.00 | 0.00 | 0.0000 | 0.0982 | 0.0982 | 0.0000 |
| ARA Fatty Acid Composition, (g) | 0.209 | 0.211 | 0.0000 | 0.207 | 0.0000 | 0.0000 |
| Target Fat Weight (g) | 6.56 | 6.56 | 6.56 | 5.91 | 5.91 | 5.91 |
| Target DHA Weight (g) | 0.00 | 0.00 | 0.0000 | 0.0296 | 0.0296 | 0.0000 |

-continued

| Ingredient | Example 8 | Example 13 | Blank 1 | Example 14 | Example 16 | Blank 2 |
|---|---|---|---|---|---|---|
| Target ARA Weight (g) | 0.0656 | 0.0656 | 0.0000 | 0.0591 | 0.0000 | 0.0000 |
| Whole Milk Powder (g) | 21.88 | 21.88 | 21.88 | 19.70 | 19.70 | 19.70 |
| Skimmed Milk Powder (g) | 11.38 | 11.38 | 11.38 | 13.55 | 13.55 | 13.55 |
| Water (g) | 216.50 | 216.50 | 216.80 | 216.50 | 216.70 | 216.80 |
| Solution Volume (mL) | 250 | 250 | 250 | 250 | 250 | 250 |

Preparation of a Skim Milk Based Vanilla Breakfast Drink Fortified with Na-DHA Composition to Provide 25% of RDA for DHA

| | % Weight, PUFA (DHA) | Target DHA Weight | DHA (g) | Solution Volume, Cold Fat-free milk (mL) | Solution Weight, Cold Fat-free milk (g) | Vanilla Drink Mix Powder Weight (g) |
|---|---|---|---|---|---|---|
| Na-DHA Fortified Breakfast Drink | 30.10 | 0.0625 | 0.205 | 240 | 285 | 36 |

The table below shows calculated amounts protein, fat, and carbohydrate of a commercially available milk-based drink both prior to and after inclusion of a 40% by weight Na-ARA fatty acid composition (Example 11). The calculations were performed such that each infant formula or drink would be fortified with 1% by weight arachidonic acid (ARA) based on the fat content of the drink or infant formula powder. The initial weight of each drink is 100 g.

| | Neosure Infant Formula, Weight % Composition | | Similac Advance, Weight % Composition | | Nestle CarnationBreakfast Drink, Weight % Composition | |
|---|---|---|---|---|---|---|
| Nutrient Component | "As is" | with fortification | "As is" | With fortification | "As is" | With fortification |
| Protein | 2.0 | 2.0 | 1.4 | 1.4 | | |
| Fat | 4.0 | 4.10 | 3.7 | 3.79 | 2.4 | 2.46 |
| Carbohydrate | 7.3 | 7.3 | 7.1 | 7.1 | | |
| Total Weight Per Cent Milk Solids in the Drink | 13.3 | 13.4 | 12.2 | 12.3 | 13.3 | 13.4 |
| Weight of Fatty Acid Salt Composition Used to Fortify | | 0.10 g | | 0.09 g | | 0.05 g |

Results Demonstrating Instant Dispersion

There is a significant benefit in using the sodium and potassium salt compositions described above, compared to the traditionally microencapsulated triglycerides used in the existing prior art (examples of which are noted in the Background Section). The beneficial properties of our fatty acid salt compositions arise mainly from the higher water solubility and emulsifiability of the contained sodium and potassium fatty acid salts. The microencapsulated triglycerides of the prior art lack these attractive properties.

The disclosed sodium and potassium fatty acid salt compositions have the very desirable property of being substantially instantly soluble or dispersible in water by stirring or shaking for a very short time (i.e., in less than 1 minute, and preferably less than about 30 seconds). This property is a prerequisite for dry powders that must be reconstituted into a drinkable form before using. Usually the act of reconstitution of the fatty acid composition powder occurs in simple water, or in a milk-based drink. Typical drinks that require this reconstitution prior to use notably include powdered infant formula, breakfast drink powders, and meal replacement drink powders.

Further, it is evident from the emulsifying power of these salts that their significant aqueous solubility confers on them the capacity for dispersing even more fatty acid salt or triglyceride species in aqueous medium, in the form of stable salt dispersions, or oil-in-water emulsions.

Therefore, our fatty acid composition provides monovalent salts of long-chain polyunsaturated fatty acids (LCPU-FA's) of 18-carbon chains or longer, which are used as delivery systems for fortifying water or milk-based nutritional drinks with nutritionally important omega-3's and omega-6's. The dispersabitliy of the fatty acids surprisingly exceeded the expected dispersion of the fatty acids in liquid. This is true of the PUFAs that have four or more double bonds.

Analysis of the dissolution time of the dried powder was performed within 1-2 days of preparation. The dried powders were coarsely ground; however, particle sizes were not measured.

For the dissolution time analysis, 13 mg of the dried powder was mixed with 10 g of deionized water in a sealed vial at 25° C. The vial was then shaken by hand. The dissolution time was the time required for the last visible particle to fully dissolve.

Upon dissolution, the dried powders typically produced colorless solutions that were clear to slightly hazy. The solution remained stable for many hours i.e. no particulates settled out of the solution.

For comparison, a sodium arachidonic acid (ARA) component and sodium docosahexaenoic acid (DHA) component (i.e., Examples 18 and 19) were prepared without any additives and the dissolution times were measured. The pure sodium arachidonic acid (ARA) component (Powder Example 18) and sodium docosahexaenoic acid (DHA) component (Powder Example 19) consistent with the other formulations were easily dispersed. The following tables compare results.

When compared to the pure sodium arachidonic acid (ARA) component, the addition of a phosphate salt to the formulation generally decreased the dissolution time.

|  | Total percent of sodium fatty acid | Percent phosphate | Dissolution Time |
|---|---|---|---|
| Powder Ex. 18 | 100 | 0 | ~1 min |
| Powder Ex. 11 | 89 | 6 | 47.9 seconds |
| Powder Ex. 12 | 85 | 10 | 33.2 seconds |
| Powder Ex. 13 | 76 | 20 | 22.7 seconds |

The following examples (sodium ARA) illustrate the dissolution rate with changes in the formulation.

|  | Percent Phosphate | Percent Protein | Percent Carbohydrates | Dissolution Time |
|---|---|---|---|---|
| Powder Ex. 17 | 6 | 0 | 5 (Rice bran extract) | 3.3 seconds |
| Powder Ex. 14 | 20 | 0 | 5 (Maltodextrin) | 16.9 seconds |
| Powder Ex. 13 | 20 | 0 | 0.8 (Rice bran extract) | 21.8 seconds |
| Powder Ex. 8 | 20 | 0 | 0 | 25.5 seconds |

The following examples of sodium DHA powders illustrate the dissolution rate with changes in the formulation.

|  | Percent Phosphate | Percent Protein | Percent Carbohydrates | Dissolution Time |
|---|---|---|---|---|
| Powder Ex. 19 | 0 | 0 | 0 | 42.0 seconds |
| Powder Ex. 3 | 5 | 25 (Na Caseinate) | 2 (Maltodextrin) | 32.4 seconds |
| Powder Ex. 4 | 5 | 25 (Nonfat Milk Powder) | 2 (Maltodextrin) | 25.4 seconds |
| Powder Ex 10 | 25 | 0 | 0 | 24. seconds |
| Powder Ex. 15 | 30 | 0 | 2 | 24.5 seconds |

Use of Fatty Acid Salt to Enhance Dispersability of Co-Salts

When the fatty acid composition is mixed in liquid that contains a low concentration of calcium ions, it is believed that the fatty acid component (Na-ARA, Na-DHA, etc.) reacts with calcium ions (which are present in liquid milk or in milk powder) to produce a calcium co-salt of the fatty acid and phosphate, such as described in U.S. Pat. Nos. 8,178,707 and 8,378,131 which are incorporated herein by reference.

It is believed that the simple fatty acid salt of the composition enhances the instantizability of the fatty acid composition. As shown by the examples below, the co-salt disclosed in U.S. Pat. Nos. 8,178,707 and 8,378,131 does not emulsify in liquid. However, when the co-salt is combined with a simple fatty acid salt, the complete composition (co-salt and simple fatty acid salt) emulsify or disperse in the liquid.

(A) Working Example Using K-Salts of PUFA's to Emulsify "Calcium Phosphate-PUFA Co-Salt" of the U.S. Pat. Nos. 8,178,707 and 8,378,131:
1. Charge to 1-L reaction flask, equipped with Teflon paddle stirrer, $N_2$-inlet, and jacket for heating and cooling: 500-mL degassed, deionized water
2. Using the heating medium in the jacket, heat to 40° C. Next add 9.30 g mixed "ARA-rich free fatty acids". With rapid stirring, add sufficient 45% KOH(aqueous) to dissolve the free fatty acids and resulting in a final pH of 10.0-10.8 This should require about 3.7 g of the 45% KOH.
3. In a separate container, make up a solution of 0.96 g $K_2HPO_4$ in 150-mL degassed, deionized water.
4. Mix the two solutions well. Then, with vigorous stirring add dropwise a total of 6.00 g of a 21.6% $CaCl_2$ solution to the mixture.
5. After the addition of the $CaCl_2$ solution has been completed, dilute with an additional 200-mL degassed, deionized water. Then stir under high-shear agitation sufficient time to completely emulsify. Additional triglyceride oils (20-25 g) may be added before the high-shear stir period to form a stable oil-in-water emulsion.

Result:

A similar experiment with only the "Calcium Phosphate-PUFA Co-Salt" present with none of the K-salts of the PUFA acids results in a slurry of filterable solids instead of the oil-in-water emulsion/dispersion obtained above. The filterable solids are "Calcium Phosphate-PUFA Co-Salts".

(B) Working Example Using K-Salts of PUFA's to Emulsify "Calcium Phosphate-PUFA Co-Salt" of the U.S. Pat. Nos. 8,178,707 and 8,378,131 Along with "Simple Calcium PUFA Salt":
1. Charge to 1-L reaction flask, equipped with Teflon paddle stirrer, $N_2$-inlet, and jacket for heating and cooling: 150-mL degassed, deionized water
2. Using the heating medium in the jacket, heat to 40° C. Next add 23.5 g mixed "ARA-rich free fatty acids". With rapid stirring, add 0.92 g 45% KOH, (aqueous) to partially dissolve the free fatty acids.
3. Then add 3.10 g $Ca(OH)_2$. Stir well for 1-2 minutes.
4. In a separate container, make up a solution of 2.78 g $K_2HPO_4$ in 150-mL degassed, deionized water.
5. Mix the two solutions well, by adding the fatty acid containing mixture to the $K_2HPO_4$ solution.
6. Stir vigorously the two combined solutions for 2-3 hours at 40° C.-50° C. until the pH is stable. Then stir under high-shear agitation sufficient time to completely emulsify. Additional triglyceride oils (20-25 g) may be added before the high-shear stir period to form a stable oil-in-water emulsion.

Result:

A similar experiment with only the "Calcium Phosphate-PUFA Co-Salt" and the "Simple Calcium PUFA Salt" present with none of the K-salts of the PUFA acids results in a slurry of filterable solids instead of the oil-in-water emulsion/dispersion obtained above. The filterable solids are "Calcium Phosphate-PUFA Co-Salts" and "Simple Calcium PUFA Salts".

(C). Working Example Using Na-Salts of PUFA's to Emulsify "Calcium Phosphate-PUFA Co-Salt" of the U.S. Pat. Nos. 8,178,707 and 8,378,131:
1. Charge to 1-L reaction flask, equipped with Teflon paddle stirrer, $N_2$-inlet, and jacket for heating and cooling: 500-mL degassed, deionized water
2. Using the heating medium in the jacket, heat to 40° C. Next add 9.30 g mixed "ARA-rich free fatty acids". With rapid stirring, add sufficient 50% NaOH(aqueous) to dissolve the free fatty acids and resulting in a final pH of 10.0-10.8 This should require about 2.4 g of the 50% NaOH.

3. In a separate container, make up a solution of 0.96 g $K_2HPO_4$ in 150-mL degassed, deionized water.
4. Mix the two solutions well. Then, with vigorous stirring add dropwise a total of 6.00 g of a 21.6% $CaCl_2$ solution to the mixture.
5. After the addition of the $CaCl_2$ solution has been completed, dilute with an additional 200-mL degassed, deionized water. Then stir under high-shear agitation sufficient time to completely emulsify. Additional triglyceride oils (20-25 g) may be added before the high-shear stir period to form a stable oil-in-water emulsion.

Result:

A similar experiment with only the "Calcium Phosphate-PUFA Co-Salt" present with none of the Na-salts of the PUFA acids results in a slurry of filterable solids instead of the oil-in-water emulsion/dispersion obtained above. The filterable solids are "Calcium Phosphate-PUFA Co-Salts".

Conclusion: The enhanced dispersibility demonstrated by the long chain PUFA (LCPUFA) salts can be used to disperse and emulsify the co-salts disclosed in the Jost Chemical Co.'s U.S. Pat. Nos. 8,178,707 and 8,378,131. The fatty acid concentration levels thereby obtained can exceed the otherwise expected levels The dispersibility tests show that a spray dried fatty acid (such as a spray dried sodium and potassium salts of ARA and DHA) in powder form disperses without the need for additional components to the composition. Thus, in such instances, the fatty acid composition comprises only the fatty acid salt.

Bioavailability

The fatty acid compositions have a higher bioavailability of the fatty acids than do currently available microencapsulated triglycerides, such as noted above. Generally, when fat or lipid boluses are swallowed, they must be broken down and emulsified with the help of bile salts and other amphipathic molecules to form small emulsion droplets. This increases the surface area sufficiently so that water-soluble lipase can begin to hydrolyze the fatty acids from the triglycerides. In the case of both infant formula products (whether made with our above-noted compositions or a triglyceride source) this hydrolysis can begin relatively rapidly as the powder particles are already small. (Parada Ji, Aguilera J M. Food microstructure affects the bioavailability of several nutrients. J Food Sci. 2007 March; 72(2):R21-32.) As the mixture moves from the stomach to the duodenum, the enzyme concentration is markedly increased by pancreatic lipase and the rate of hydrolysis is increased.

In the formula made with a triglyceride source, the enzymatic process cleaves the fatty acids from the triglycerides leaving intact only the monoglycerides which enter into micelles and become suspended in solution. Micellular formation occurs because ARA and the other long chain fatty acid molecules and the monoglycerides in the added fat are insoluble in water (Handbook of Chemistry and Physics, $84^{th}$ Edition 2003-2004 CRC Press, page 7-6) and are only solubilized by their incorporation into micelles. Since the ARA-glycerides are minor components of both the fats and the gastric medium, the micelle composition itself consists mainly of endogenous bile salts, phospholipids, cholesterol, vitamins and the other fatty acids.

In the case of the formula made with the above-noted compositions, the digestion process is similar with one exception. The fatty acids from the sodium salts, once released from the powder particles, are immediately reconstituted into the free acids by the strong stomach acid. For example: the protonation of the ARA anion is: $ArA^{-}+H^{+}\rightarrow$ [$ARA^0$] or ARA, and the high acid concentration drives the reaction to the right. The rates of acid: base reactions involve only proton transfers and are well known to be extremely fast (the order of $10^{-12}$ sec). ((a) RP. Bell, (1959) 13: 168-182. "The rates of simple acid-base reactions," Q. Rev. Chem. Soc., 1959, 13, 169-182, and (b) EF Caldin (2001) "The Mechanisms of Fast Reactions in Solution", page 11, Table 1.2 Distributed by Jos Press 5795G Burke Center Parkway, Burke Va. 22015). The diffusion constants of molecules in water are on the order of $10^{-6}$ s/$cm^2$. The fastest possible time for a single molecule to aggregate into a micelle 10 nm in diameter, using the Einstein diffusion formula, is $\tau=\lambda^2/6D$. Thus, the noted rates are much faster than the subsequent aggregation of released fatty acids into micelles which can take several microseconds or longer. Because the formation of the unionized fatty acid from its salt is so rapid, this reaction cannot affect the overall digestion process as long as sufficient acid is present.

A key enzyme required for the metabolism of triglycerides is lipase, most of which is secreted by the pancreas. At birth this enzyme is not fully expressed and does not reach full development until six months of age. In the interim, while there are compensating mechanisms, the amount of available lipase is a limiting factor in the hydrolysis of triglycerides. (Koldovsky O. (1998) Digestive-Absorption Functions in Fetuses, Infants and children, Chapter 128 p 1404 in "Fetal and Neonatal Physiology" 2nd Ed Vol 2. R A Polin and W W Fox, W.B Saunders Co. Philadelphia.) The sodium salts of the fatty acids do not require hydrolysis once they are converted into the free acid, so this limitation does not exist for our fatty acid composition. Thus, it is expected that the fatty acid composition will break down in the stomach, such that the fatty acid component becomes bioavailable in the stomach.

Stability

As a general matter, the high sensitivity of omega fatty acids to oxygen is related to their molecular structure and physical state. Polyunsaturated fatty acids (PUFAs) such as eicosapentaenoic acid (EPA), docosahexaenoic acid (DHA), and arachidonic acid (ARA) contain more than two double bonds in the cis-configuration. As the number of double bonds within a PUFA increases, the fatty acid becomes more susceptible to oxidative degradation. The physical state (i.e., liquid or solid) determines the rate of diffusion of oxygen throughout the substance. Diffusion of oxygen through a liquid occurs more rapidly than through a solid matrix. Thus, oxygen saturation occurs faster in liquids than in solids, allowing oxidation to occur more rapidly. ((a) Hsu H, Trusovs S, Popova T., Preparation of Fatty Acids in Solid Form; (b) U.S. Pat. No. 8,203,013 (Jun. 19, 2012)). For this reason, solids generally are considered more stable toward oxidation than liquids.

Fatty Acid Composition Example Nos. 2 and 9 (which both contained an Na-ARA salt) were placed on stability studies under real time conditions and accelerated conditions in metalized and low density polyethylene (LDPE) storage bags. The stability of the compositions was determined by measuring the level of oxidative degradation of the fatty acid composition. For the real time conditions, the powder compositions were stored at 25° C. and 60% R.H.; and for the accelerated conditions, the powder compositions were stored at 40° C. and 75% R.H. These conditions are designated by the Q1A guideline produced by the International Conference On Harmonisation Of Technical Requirements For Registration Of Pharmaceuticals For Human Use (hereinafter, ICH Q1A). Measurements of oxidative degradation were performed using GC analysis, Peroxide values and Anisidine values at selected time intervals. Real time storage conditions and accelerated storage conditions were both run for 13 months. Under the ICH Q1A, 13 months under the accelerated conditions simulates 4 years of storage. The data from the studies is tabulated in Tables VA.

The data below represents data collected from ongoing stability studies on two Na-arachidonate salt formulations (Composition Example Nos. 2 and 9, as noted above). Two packaging forms were used: (1) metalized bags, which is the preferred packaging material, and (2) low density polyethylene (LDPE) bags which function as positive controls. Both "long-term, room temperature" and "accelerated conditions" were studied, with the results of the long term, room temperature study being tabulated in Tables VA and VB below and the results of the accelerated study being tabulated in Table VIA and VIB below.

Long Term Real Time Study

In the real time stability study, Powder Example 2 (comprised of 70% PUFA (43.1% ARA), 20% disodium hydrogen phosphate, 5% Maltrin OD M550 (a maltodextrin available from Grain Processing Corporation of Muscatine, Iowa), 3% sodium ascorbate, 2% trisodium citrate) and Powder Example 9 (comprised 75% PUFA (43.1% ARA), 20% Disodium hydrogen phosphate, 3% sodium ascorbate, 2% trisodium citrate) were stored at 25° C. (essentially room temperature) and 60% R.H. The results are tabulated in Tables VA and VB. The results show that the fatty acid compositions oxidized very little over a 12 month period, although the oxidation for the samples stored in the LDPE bags was greater than for the samples stored in the metalized bags. This was due to the greater air permeability of the LDPE bag relative to the metalized bag.

TABLE VA

| Long-Term Real Time Conditions | | | | |
|---|---|---|---|---|
| Composition 9 | Metalized Bag | | LDPE Bag | |
| Months | 0 | 12 | 0 | 12 |
| ARA (% of Total Fatty Acid) | 36.78 | 36.07 | 36.78 | 33.17 |

TABLE VA-continued

| Long-Term Real Time Conditions | | | | |
|---|---|---|---|---|
| Composition 9 | Metalized Bag | | LDPE Bag | |
| Peroxide Value | 0 | 0 | 0 | 6.6 |
| Anisidine Value | 0 | 3.61 | 0 | N/A |

TABLE VB

| Long-Term Real Time Conditions | | | | |
|---|---|---|---|---|
| Composition 2 | Metalized Bag | | LDPE Bag | |
| Months | 0 | 12 | 0 | 12 |
| ARA (% of Total Fatty Acid) | 33.92 | 33.51 | 33.92 | 31.45 |
| Peroxide Value | 0 | 6.6 | 0 | 12.3 |
| Anisidine Value | 0 | N/A | 0 | n/a |

In the accelerated storage study Powder Example 2 (comprised of 70% PUFA (43.1% ARA), 20% disodium hydrogen phosphate, 5% Maltrin OD M550, 3% sodium ascorbate, 2% trisodium citrate) and Powder Example 9 (comprised 75% PUFA (43.1% ARA), 20% Disodium hydrogen phosphate, 3% sodium ascorbate, 2% trisodium citrate) were stored at 40° C. and 75% R.H. The results are tabulated in Tables VIA and VIB below. As with the real-time/room temperature study, the fatty acid compositions oxidized very little over a 13 month period, although the oxidation for the samples stored in the LDPE bags was greater than for the samples stored in the metalized bags. Thirteen months of an accelerated study is generally considered to correspond to about 4 years (48 months) of real time storage at room temperature. Thus, it is expected that the fatty acid compositions would be shelf storage stable for at least 36 months, and for as long as 48 months (and possibly longer).

TABLE VIA

| Accelerated Study | | | | | | | |
|---|---|---|---|---|---|---|---|
| Composition 9 | Metalized Bag | | | | LDPE Bag | | |
| Months | 0 | 1 | 2 | 13 | 0 | 1 | 2 |
| ARA (% Total Fatty Acid) | 36.78 | 36.77 | 36.94 | 36.74 | 36.78 | 37.09 | 33.81 |
| Peroxide Value | 0 | 0 | 0 | 0 | 0.00 | 15.00 | 12.70 |
| Anisidine Value | 0 | 1.14 | 3.12 | 1.6 | 0.00 | 13.06 | 28.23 |

TABLE VIB

| Accelerated Study | | | | | | | |
|---|---|---|---|---|---|---|---|
| Composition 2 | Metalized Bag | | | | LDPE Bag | | |
| Months | 0 | 1 | 2 | 13 | 0 | 1 | 2 |
| ARA (% Total Fatty Acid) | 33.92 | 34.35 | 34.39 | 33.50 | 33.92 | 33.24 | 33.11 |

TABLE VIB-continued

Accelerated Study

| Composition 2 | Metalized Bag | | | | LDPE Bag | | |
|---|---|---|---|---|---|---|---|
| Months | 0 | 1 | 2 | 13 | 0 | 1 | 2 |
| Peroxide Value | 0 | 0 | 0 | 0 | 0 | 8.50 | 6.70 |
| Anisidine Value | 0 | 1.39 | 1.17 | 2.11 | 0 | 5.43 | 12.23 |

In further studies, the stability of the solid powdered fatty acid compositions were compared to a liquid state triglyceride-containing PUFA. It would be expected that a PUFA-containing triglyceride (Tg) liquid would exhibit more rapid oxidative degradation than a similar solid PUFA-Na salt.

To test this hypothesis, experimental data was collected on stability experiments run on these liquid and solid samples. In the comparison test, the oxidation of a liquid triglyceride fish oil was compared to that of solid sodium arachidonate salt formulations of Composition Example Nos. 2 and 9.

The experiment compared liquid fish oil, having a PUFA concentration (EPA+DHA content) of about 30% to that of solid sodium arachidonate salt formulations of Composition Nos. 2 and 9 with a very similar 30% PUFA concentration. The PUFA concentration in the PUFA sodium salt formulation is found by normalizing the PUFA concentration to the level of PUFA salt in the formulation, i.e., (0.75)×(40)=30%. The remainder of the formulated sodium salt product is comprised of dibasic sodium phosphate, sodium citrate, and sodium ascorbate.

The test period ran for one month at accelerated conditions of 40° C. and 75% relative humidity. At the end of the one-month period, the degree of oxidation was measured employing commonly used analytical method from the U.S. Pharmacopoeia, namely the "peroxide value" and the "anisidine value". The composite of these two determinations was used to express the "TOTOX Value", also a commonly used oxidation metric from the U.S. Pharmacopoeia. The lower the TOTOX value, the lower the degree of oxidation that occurred.

The results are tabulated in Tables VII and VIII below. Table VII includes the results for the samples packaged in metalized bags. These bags have essentially no $O_2$-transfer rate or moisture transfer rate. Table VIII shows the results for the samples contained in low-density polyethylene (LDPE) bags. This bag is meant to be a positive control, allowing some $O_2$ and water vapor transmission into the sample.

TABLE VII

Samples run for 1 month in metalized bags at accelerated conditions (40° C., 75% R.H.)

| | | Time 0 | | | 1 Month | | |
|---|---|---|---|---|---|---|---|
| Sample | Sample Origin | Peroxide Value | Anisidine Value | TOTOX | Peroxide Value | Anisidine Value | TOTOX |
| Liquid Tg | ONC oil | 0 | 4 | 4 | 3 | 6 | 11 |
| A: Solid ARA-Na | M. alpina oil | 0 | 0 | 0 | 0 | 1 | 1 |
| B: Solid ARA-Na | M. alpine oil | 0 | 0 | 0 | 0 | 1 | 1 |

TABLE VIII

Samples run for 1 month in LDPE bags at accelerated conditions (40° C., 75% R.H.)

| | | Time 0 | | | 1 Month | | |
|---|---|---|---|---|---|---|---|
| Sample | Sample Origin | Peroxide Value | Anisidine Value | TOTOX | Peroxide Value | Anisidine Value | TOTOX |
| Liquid Tg | ONC oil | 0 | 4 | 4 | 377 | 555 | 1309 |
| A: Solid ARA-Na | M. alpina oil | 0 | 0 | 0 | 15 | 13 | 43 |
| B: Solid ARA-Na | M. alpine oil | 0 | 0 | 0 | 9 | 5 | 22 |

The large difference in TOTOX values measured from samples in the LDPE bag demonstrates that the solid/powder fatty acid composition degrades at a substantially lower rate than the liquid triglyceride. The difference between the results of the metalized and LDPE bags demonstrates the effect the type of bag can have on the oxidation of the sample. As seen, the results from the samples packaged in the metallized bags show clearly that no oxidative degradation occurs if the solid Na-arachidonate salts are stored and packaged in these bags.

The results in Table VIII strongly and clearly demonstrate the superior oxidative stability of the solid state Na-arachidonate salt formulations compared to the liquid triglyceride.

The following conclusions can be drawn from the studies outlined above:

- in the preferred metalized bag packaging, acceptable results are observed under both long-term and room temperature conditions up to twelve months' time period, and accelerated conditions up to 13-months' time period;
- Packaging form is clearly important. It appears that proper packaging can guarantee stability of the PUFA salt under the conditions and time studied
- While packaging is important, it is even more significant to note that the salt form of the PUFA has clear oxidative stability advantages over the triglyceride form.

As can be seen from the results above, the noted compositions exhibited excellent long term stability (i.e., shelf life). Although the long term stability study only monitored the two compositions for 12 months, it is expected that the composition would be stable for up to 18 months and even up to 36 months. Testing further predicts stability for up to 48 months.

In view of the above, it will be seen that we have developed a fatty acid composition that is simple to produce and does not require micro-encapsulation, as is required by currently available powder composition. The fatty acid composition is quickly and easily dissolved in a liquid by simple shaking or stirring to form a dispersion that is stable for at least several hours.

As various changes could be made in the above constructions without departing from the scope of the invention, it is intended that all matter contained in the above description or shown in the accompanying drawings shall be interpreted as illustrative and not in a limiting sense.

The invention claimed is:

1. A fatty acid composition for making fatty acid fortified nutritional products; the fatty acid composition being in powder form; the fatty acid composition comprising: a fatty acid component including a desired fatty acid chosen from the group consisting of arachidonic acid (ARA), eicosapentaenoic acid (EPA), docosapentaenoic acid (DPA), eicosatetraenoic acid, heneicosapentaenoic acid, docosahexaenoic acid (DHA), and combinations thereof, optionally at least one vitamin, a salt that is not a fatty acid salt, an optional protein source, and an optional carbohydrate source; wherein the fatty acid component consists of a monovalent simple fatty acid salt, wherein the desired fatty acid comprises at least 24 wt % of the fatty acid composition, wherein the fatty acid composition is not microencapsulated; and wherein the fatty acid composition is substantially instantizable in liquid upon stirring, shaking, or otherwise agitating in any effective manner the fatty acid composition powder in the liquid for less than one minute.

2. The fatty acid composition of claim 1 wherein if the fatty acid composition is 100% fatty acid salt, the fatty acid salt is a dried fatty acid salt.

3. The fatty acid composition of claim 1, wherein the fatty acid component is an ARA salt or a DHA salt.

4. The fatty acid composition of claim 1, wherein the fatty acid component is a sodium or potassium salt of the fatty acid.

5. The fatty acid composition of claim 1 wherein the fatty acid component is a long-chain polyunsaturated fatty acid (LCPUFA) of 18 carbons or longer.

6. The fatty acid composition of claim 5 wherein the LCPUFA contains at least four double bonds.

7. The fatty acid composition of claim 1 wherein the fatty acid component disassociates in a human stomach to be readily available for absorption within the human digestive tract.

8. The fatty acid composition of claim 1, wherein the fatty acid component comprises one or more monovalent cations chosen from the group consisting of sodium, potassium, ammonium and free base forms of choline, lecithin, alanine, arginine, asparagine, aspartic acid, cysteine, glutamic acid, glutamine, glycine, ornithine, proline, selenocysteine, serine, tyrosine, histidine, isoleucine, leucine, lysine, methionine, phenylalanine, threonine, tryptophan, and valine, and combinations thereof.

9. The fatty acid composition of claim 1, wherein the fatty acid composition is substantially free of triglycerides.

10. The fatty acid composition of claim 1, wherein the fatty acid composition comprises up to about 3% by weight vitamin, the at least one vitamin being chosen from the group consisting of vitamin C (ascorbic acid), vitamin E, vitamin A, vitamin D, vitamin K, vitamin B12, choline, folic acid, thiamine, riboflavin, carotenoids, niacin, pantothenic acid, biotin, mixed isomers of tocopherol, salts and their derivatives and combinations thereof.

11. The fatty acid composition of claim 10 wherein the at least one vitamin comprises vitamin C, vitamin E, their salts and derivatives, and combinations thereof.

12. The fatty acid composition of claim 10 wherein the vitamin source is an ascorbate salt.

13. The fatty acid composition of claim 1, wherein the salts are chosen from salts of citric acid, citric acid derivatives, phosphates, and combinations thereof.

14. The fatty acid composition of claim 13 wherein the phosphates are chosen from dibasic sodium phosphate, tetrasodium diphosphate, tricalcium phosphate, dibasic potassium phosphate, tetrapotassium diphosphate, ammonium phosphate salt, and combinations thereof.

15. The fatty acid composition of claim 1, wherein the composition includes up to about 30% by weight of a protein source, the protein source being chosen from the group consisting of skim milk powder, whole milk powder, nonfat milk powder, caseinates, whey, soy protein isolate, pea protein isolate, their derivatives, and combinations thereof.

16. The fatty acid composition of claim 13, wherein the caseinate is chosen from the group consisting of casein and salts thereof and combinations thereof.

17. The fatty acid composition of claim 16 wherein the caseinate salt is selected from the group consisting of sodium caseinate, calcium caseinate, potassium caseinate, and combinations thereof.

18. The fatty acid composition of claim 1 wherein composition includes up to about 5% by weight of a carbohydrate source, the carbohydrate source being selected from the group consisting of maltodextrin, sugar, modified sugar, starch, modified starch, glucose, derivatives thereof, and combinations thereof.

19. The fatty acid composition of claim 1, wherein the fatty acid composition comprises by weight about 10% to about 98% fatty acid component; about 1% to about 4% vitamins, about 1% to about 50% salts, 0% to about 40% protein, and about 0% to about 70% carbohydrates.

20. The fatty acid composition of claim 19, wherein the fatty acid composition comprises about 20% to about 50% by weight of a desired fatty acid.

21. The fatty acid composition of claim 19, wherein the salt is a phosphate, and the ratio of desired fatty acid to a phosphate is about 0.3:1 to about 99:1.

22. The fatty acid composition of claim 21, wherein the ratio of desired fatty acid to phosphate source is about 0.9:1 to about 10.4:1.

23. The fatty acid composition of claim 19, wherein the composition is about 30% by weight desired fatty acid component.

24. The fatty acid composition of claim 19, wherein the composition is about 10% by weight salts.

25. The fatty acid composition of claim 19, wherein the composition is about 5% carbohydrates.

26. The fatty acid composition of claim 19, wherein the composition is about 20% by weight protein.

27. The fatty acid composition of claim 19, wherein the composition is about 3% to about 4% by weight vitamins.

28. The fatty acid composition of claim 1, wherein the fatty acid composition comprises milk powder or milk substitute powder; said milk powder or milk substitute powder being the protein source, wherein said fatty acid composition is added to water to form a fatty acid fortified milk-based or milk substitute-based beverage.

29. The fatty acid composition of claim 28, wherein the fatty acid composition is about 25% by weight milk powder or milk substitute powder.

30. A fatty acid composition for making fatty acid fortified nutritional products; the fatty acid composition being in powder form; the fatty acid composition comprising by weight: about 10% to about 89% simple fatty acid component, about 1% to about 4% vitamins, about 2.4% to about 50% salts which are not fatty acid salts, 0% to about 70% carbohydrate, and 0% to about 40% protein; the fatty acid component consisting of a monovalent simple fatty acid salt; wherein the fatty acid composition is not microencapsulated and wherein the fatty acid composition is substantially instantizable in liquid upon stirring, shaking, or otherwise agitating in any effective manner the fatty acid composition powder in the liquid for less than one minute.

31. A fatty acid fortified milk product comprising milk or a milk substitute and the fatty acid composition of claim 30.

32. The fatty acid fortified milk product of claim 31, wherein the fortified milk product contains triglycerides, and the triglycerides are dispersed in the milk product.

33. The fatty acid component fortified milk product of claim 31, wherein the milk substitute is infant formula.

34. The fatty acid fortified milk product of claim 31, wherein the fortified milk product is about 10% to about 20% by weight milk powder or milk substitute powder.

35. The fatty acid fortified milk product of claim 33, wherein both the infant formula and the fatty acid composition are in powder form.

36. The fatty acid fortified milk product of claim 33 wherein the fortified milk product has a fat content of between about 2% and about 5%.

37. The fatty acid fortified milk product of claim 36, wherein the fatty acid composition comprises between about 20% and about 50% by weight desired fatty acid component.

38. The fatty acid fortified milk product of claim 33 wherein the fatty acid component is an ARA or DHA salt; said ARA or DHA salt being present in the fatty acid fortified milk product in an amount approximately equal to the amount of ARA or DHA in human breast milk.

39. A method of preparing a fatty acid fortified infant formula, the method comprising:
adding the fatty acid composition of claim 30 to an infant formula in an amount sufficient to provide a desired fatty acid in an amount such that the fatty acid content of the fatty acid fortified infant formula corresponds to the amount of the desired fatty acid present in human breast milk; and
stirring, shaking, or otherwise agitating the infant formula with the powdered fatty acid composition in any effective manner for less than one minute to accomplish mixing the infant formula with the fatty acid composition, whereby a stable dispersion of the fatty acid composition in the infant formula is formed.

40. A method of fortifying a milk or milk substitute with a desired fatty acid component comprising combining the fatty acid composition of claim 28 with a milk or milk substitute and dispersing the fatty acid composition in a liquid by stirring, shaking, or agitating in any effective manner to accomplish mixing.

41. The method of claim 40, wherein the milk or milk substitute is a liquid milk or milk substitute such that the liquid is the milk or milk substitute.

42. The method of claim 40, wherein the milk or milk substitute is a milk powder or milk substitute powder and wherein said liquid is water; said method comprising adding the milk powder or milk substitute powder and the fatty acid powder to the water.

43. The method of claim 40, wherein the milk powder or milk substitute powder and the fatty acid composition are added to the liquid at the same time.

44. A fatty acid fortified infant formula composition comprising infant formula having milk solids and the fatty acid composition of claim 30; the fatty acid fortified infant formula comprising a sufficient amount of the fatty acid component being such that the fatty acid fortified infant formula has a fat content of between about 2% and about 5%; the fatty acid composition being between about 20% and about 50% by weight of the desired fatty acid component; and wherein the fortified infant formula has a fatty acid component to milk solids ratio corresponding to the fatty acid to milk solids ratio of human breast milk.

45. A method of producing a nutritional supplement coprising the fatty acid composition of claim 30; the method comprising:
preparing an aqueous mixture containing the fatty acid composition; and
spray drying the mixture to form a powder of the fatty acid composition;
whereby, the fatty acid composition powder is readily dispersed in liquid to form a stable suspension in the liquid.

46. The method of claim 45 wherein the fatty acid composition further includes a vitamin source, a salt, and optionally additional nutrients, and combinations thereof; the method including either:
(1) dry mixing selected ingredients with the fatty acid component after the fatty acid component has been spray dried; or
(2) including selected ingredients in the aqueous mixture and spray drying the fatty acid component and ingredients together.

47. The method of claim 45 including preparing the fatty acid component by saponification of a triglyceride or of a fatty acid ester with an alkaline metal hydroxide.

48. The method of claim 47 wherein the alkaline metal hydroxide is chosen from the group consisting of sodium hydroxide and potassium hydroxide, and combinations thereof.

49. The fatty acid composition of claim 1 wherein the fatty acid composition may comprise by weight about 63% to about 90% fatty acid component; about 0.5% to about 3% vitamins; about 0.5% to about 32% inorganic salts wherein about 0% to about 32% of the inorganic salts comprise phosphate salts; 0% to about 25% of a protein, and 0% to about 30% carbohydrates.

50. A fatty acid composition for making fatty acid fortified nutritional products; the fatty acid composition being in powder form; the fatty acid composition comprising:
a) about 56% to about 89% by weight of a fatty acid component, the fatty acid component being in the form of a fatty acid salt, the fatty acid component being derived from a fatty acid source comprised of multiple fatty acids and including a desired fatty acid; wherein the desired fatty acid comprises about 26% to about 40% by weight of the fatty acid component; the desired fatty acid being chosen from the group consisting of arachidonic acid (ARA), eicosapentaenoic acid (EPA), docosapentaenoic acid (DPA), eicosatetraenoic acid, heneicosapentaenoic acid, docosahexaenoic acid (DHA), and combinations thereof;
b) about 2.4 to about 31% of a salt that is not a fatty acid salt;
c) about 1% to about 4% by weight vitamin;
d) 0% to about 38% by weight protein, and
e) 0% to about 5% carbohydrate;
wherein the fatty acid composition is not microencapsulated; and wherein the fatty acid composition is substantially instantizable in liquid upon stirring, shaking, or otherwise agitating in any effective manner the fatty acid composition powder in the liquid for less than one minute.

51. The fatty acid composition of claim 50 wherein the salt is a phosphate salt, the fatty acid composition comprising a desired fatty acid to phosphate ratio of about 0.9:1 to about 10.4:1.

* * * * *